US007906123B1

(12) United States Patent
Leclerc et al.

(10) Patent No.: US 7,906,123 B1
(45) Date of Patent: Mar. 15, 2011

(54) **MODIFIED *BORDETELLA* ADENYLATE CYCLASE COMPRISING OR LACKING CD11B/CD18 INTERACTION DOMAIN AND USES THEREOF**

(75) Inventors: Claude Leclerc, Paris (FR); Mohammed El-Azami El-Idrissi, Maroc (MA); Daniel Ladant, Cachan (FR); Cécile Bauche, Paris (FR); Peter Sebo, Prague (CZ); Jirina Loucka, Kladno (CZ); Radim Osicka, Prague (CZ)

(73) Assignees: Institut Pasteur, Paris (FR); Centre National de la Recherche Scientique, Paris (FR)

( * ) Notice: Subject to any disclaimer, the term of this patent is extended or adjusted under 35 U.S.C. 154(b) by 143 days.

(21) Appl. No.: 11/713,708

(22) Filed: Mar. 5, 2007

Related U.S. Application Data

(63) Continuation of application No. 11/304,590, filed on Dec. 16, 2005, now abandoned, which is a continuation of application No. PCT/EP2004/007811, filed on Jun. 18, 2004.

(30) Foreign Application Priority Data

Jun. 18, 2003 (EP) .................................. 03291486

(51) Int. Cl.
*A61K 39/02* (2006.01)
*A61K 39/00* (2006.01)
*A61K 49/00* (2006.01)
(52) U.S. Cl. .... 424/234.1; 424/9.1; 424/9.2; 424/184.1; 424/190.1; 424/278.1; 530/300; 530/350
(58) Field of Classification Search .................. 424/9.1, 424/9.2, 184.1, 190.1, 234.1, 278.1; 530/300, 530/350
See application file for complete search history.

(56) References Cited

U.S. PATENT DOCUMENTS 6,309,648 B1 * 10/2001 Betsou et al. ............. 424/203.1
2006/0159697 A1 7/2006 Leclerc et al.

FOREIGN PATENT DOCUMENTS

| EP | 0 366 549 | 5/1990 |
| EP | 1 188 446 | 3/2002 |
| WO | WO 91 08294 | 6/1991 |
| WO | WO 93 21324 | 10/1993 |

OTHER PUBLICATIONS

Westrop et al. Journal of Bacteriology, vol. 179, No. 3,. pp. 871-879, Feb. 1997).*
Osicka et al. Infection and Immunity, vol. 68, No. 1, pp. 247-256, Jan. 2000).*
International Search Report in corresponding PCT application PCT/EP2004/007811.
European Search Report in corresponding EP application EP 03 29 1486.
Osicka et al., Delivery of CD8+ T-Cell Epitopes Into Major Histocompatibitity Complex Class I Antigen Presentation Pathway by *Bordetella pertussis* Adenylate Cyclase: Delineation of Cell Invasive Structures and Permissive Insertion Sites, *Infection and Immunity*, vol. 68:1, Jan. 2000, pp. 247-256.
Westrop et al, Structure-Function Studies of the Adenylate Cyclase Toxin of *Bordetella pertussis* and the Leukotoxin of *Pasteurella haemolytica* by Heterologous C Protein Activation and Construction of Hybrid Proteins, *Journal of Bacteriology*, vol. 179:3, Feb. 1997, pp. 871-879.
Fayolle et al., Delivery of Multiple Epitopes by Recombinant Detoxified Adenylate Cyclase of *Bordetella pertussis* Induces Protective Antiviral Immunity, *Journal of Virology*, vol. 75:16, Aug. 2001, pp. 7330-7338.
Guermonprez., In Vivo receptor-Mediated Delivery of a Recombinant Invasive Bacterial Toxin to CD11c+CD8α CD11b$^{high}$ Dendritic Cells, *Eur. J. Immunol.*, vol. 32:11, Nov. 2002, pp. 3071-3081.
Betsou et al., Bifunctional Hemolysia-Adenylate Cyclase Precursor (Cyclolysin) (ACT) (AC-HLY), *EMBL/GENBANK/DDBJ Databases*, EBI Accession No. CYAA_BORBR, Database Accession No. Q57506, Created Nov. 1, 1977.
Betsou et al, Cloning and Sequence of the *Bordetella bronchiseptica* Adenylate Cyclase—Hemolysine-Encoding gene: Comparison with *Bordetella pertussis* Gene; *Gene*, vol. 162:1, Aug. 30, 1995, pp. 165-166.
Sakamoto, et al., *Bordetella pertussins* Adenylate Cyclase Toxin, *J. Biol. Chem.*, vol. 267:19, Jul. 5, 1992, pp. 13598-13602.
Guermonprez et al., The Adenylate Cyclase Toxin of *Bordetella pertussis* Binds to Target Cells via the $X_mB_2$ Integrin (CD11b/CD/18), *J. Exp. Med.*, vol. 193:9, May 7, 2001, pp. 1035-1044.
U.S. Appl. No. 11/304,590, filed Dec. 16, 2005, Non-final Office Action dated Sep. 5, 2006.
International Preliminary Report on Patentability in corresponding PCT application PCT/EP2004/007811.

* cited by examiner

*Primary Examiner* — Rodney P. Swartz
(74) *Attorney, Agent, or Firm* — Finnegan, Henderson, Farabow, Garrett & Dunner LLP

(57) ABSTRACT

The invention relates to modified *Bordetella* adenylate cyclase toxins which are deficient for CD11b/CD18 binding and to their use in the preparation of pharmaceutical composition for the treatment of whooping cough and/or for the protection against *Bordetella* infection. The invention also relates to specific fragments of *Bordetella* adenylate cyclase comprising the CD11b/CD18 interaction domain and their use, especially for targeting a molecule of interest to CD11b expressing cells.

17 Claims, 9 Drawing Sheets

Figure 1:
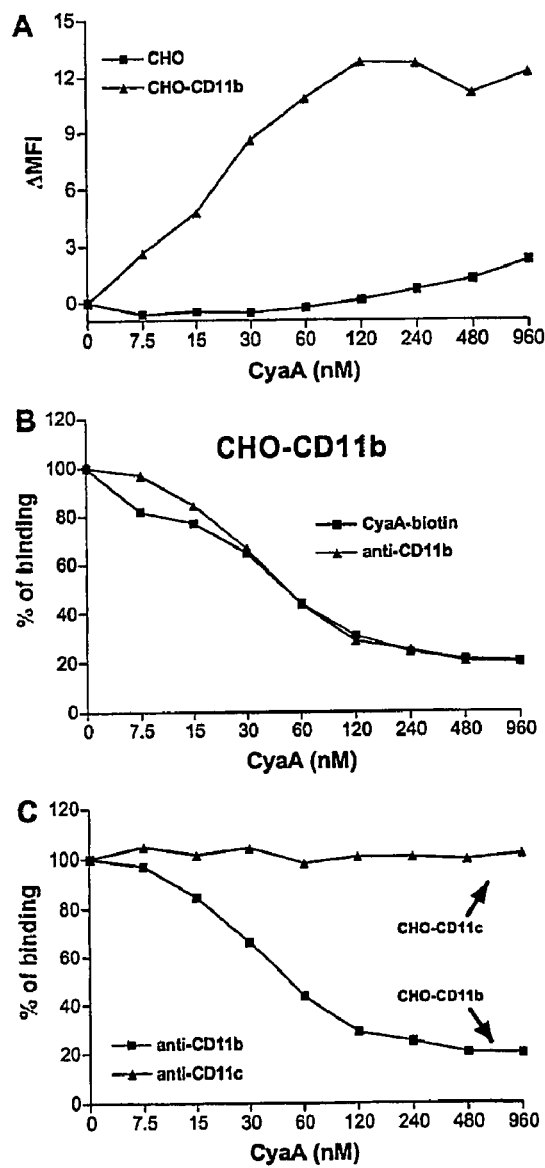

SEQUENCE LISTING

```
<160> NUMBER OF SEQ ID NOS: 12

<210> SEQ ID NO 1
<211> LENGTH: 1706
<212> TYPE: PRT
<213> ORGANISM: Bordetella pertussis

<400> SEQUENCE: 1

Met Gln Gln Ser His Gln Ala Gly Tyr Ala Asn Ala Ala Asp Arg Glu
  1               5                  10                  15

Ser Gly Ile Pro Ala Ala Val Leu Asp Gly Ile Lys Ala Val Ala Lys
             20                  25                  30

Glu Lys Asn Ala Thr Leu Met Phe Arg Leu Val Asn Pro His Ser Thr
         35                  40                  45

Ser Leu Ile Ala Glu Gly Val Ala Thr Lys Gly Leu Gly Val His Ala
     50                  55                  60
```

```
Lys Ser Ser Asp Trp Gly Leu Gln Ala Gly Tyr Ile Pro Val Asn Pro
 65                  70                  75                  80

Asn Leu Ser Lys Leu Phe Gly Arg Ala Pro Glu Val Ile Ala Arg Ala
                 85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Asn
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Ala Ala Pro Gly Val
        355                 360                 365

Pro Ser Gly Arg Ser Lys Phe Ser Pro Asp Val Leu Glu Thr Val Pro
    370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
                405                 410                 415

Leu Gly Glu Val Ser Asp Met Ala Ala Val Glu Ala Ala Glu Leu Glu
            420                 425                 430

Met Thr Arg Gln Val Leu His Ala Gly Ala Arg Gln Asp Asp Ala Glu
        435                 440                 445

Pro Gly Val Ser Gly Ala Ser Ala His Trp Gly Gln Arg Ala Leu Gln
    450                 455                 460

Gly Ala Gln Ala Val Ala Ala Gln Arg Leu Val His Ala Ile Ala
465                 470                 475                 480

Leu Met Thr Gln Phe Gly Arg Ala Gly Ser Thr Asn Thr Pro Gln Glu
```

```
                    485                 490                 495
Ala Ala Ser Leu Ser Ala Val Phe Gly Leu Gly Glu Ala Ser Ser
                500                 505                 510

Ala Val Ala Glu Thr Val Ser Gly Phe Phe Arg Gly Ser Arg Trp
                515                 520                 525

Ala Gly Gly Phe Gly Val Ala Gly Gly Ala Met Ala Leu Gly Gly Gly
                530                 535                 540

Ile Ala Ala Ala Val Gly Ala Gly Met Ser Leu Thr Asp Asp Ala Pro
545                 550                 555                 560

Ala Gly Gln Lys Ala Ala Gly Ala Glu Ile Ala Leu Gln Leu Thr
                565                 570                 575

Gly Gly Thr Val Glu Leu Ala Ser Ser Ile Ala Leu Ala Leu Ala Ala
                580                 585                 590

Ala Arg Gly Val Thr Ser Gly Leu Gln Val Ala Gly Ala Ser Ala Gly
                595                 600                 605

Ala Ala Ala Gly Ala Leu Ala Ala Leu Ser Pro Met Glu Ile Tyr
                610                 615                 620

Gly Leu Val Gln Gln Ser His Tyr Ala Asp Gln Leu Asp Lys Leu Ala
625                 630                 635                 640

Gln Glu Ser Ser Ala Tyr Gly Tyr Glu Gly Asp Ala Leu Leu Ala Gln
                645                 650                 655

Leu Tyr Arg Asp Lys Thr Ala Ala Glu Gly Ala Val Ala Gly Val Ser
                660                 665                 670

Ala Val Leu Ser Thr Val Gly Ala Ala Val Ser Ile Ala Ala Ala Ala
                675                 680                 685

Ser Val Val Gly Ala Pro Val Ala Val Val Thr Ser Leu Leu Thr Gly
                690                 695                 700

Ala Leu Asn Gly Ile Leu Arg Gly Val Gln Gln Pro Ile Ile Glu Lys
705                 710                 715                 720

Leu Ala Asn Asp Tyr Ala Arg Lys Ile Asp Glu Leu Gly Gly Pro Gln
                725                 730                 735

Ala Tyr Phe Glu Lys Asn Leu Gln Ala Arg His Glu Gln Leu Ala Asn
                740                 745                 750

Ser Asp Gly Leu Arg Lys Met Leu Ala Asp Leu Gln Ala Gly Trp Asn
                755                 760                 765

Ala Ser Ser Val Ile Gly Val Gln Thr Thr Glu Ile Ser Lys Ser Ala
                770                 775                 780

Leu Glu Leu Ala Ala Ile Thr Gly Asn Ala Asp Asn Leu Lys Ser Val
785                 790                 795                 800

Asp Val Phe Val Asp Arg Phe Val Gln Gly Glu Arg Val Ala Gly Gln
                805                 810                 815

Pro Val Leu Asp Val Ala Ala Gly Gly Ile Asp Ile Ala Ser Arg
                820                 825                 830

Lys Gly Glu Arg Pro Ala Leu Thr Phe Ile Thr Pro Leu Ala Ala Pro
                835                 840                 845

Gly Glu Glu Gln Arg Arg Thr Lys Thr Gly Lys Ser Glu Phe Thr
                850                 855                 860

Thr Phe Val Glu Ile Val Gly Lys Gln Asp Arg Trp Arg Ile Arg Asp
865                 870                 875                 880

Gly Ala Ala Asp Thr Thr Ile Asp Leu Ala Lys Val Val Ser Gln Leu
                885                 890                 895

Val Asp Ala Asn Gly Val Leu Lys His Ser Ile Lys Leu Asp Val Ile
                900                 905                 910
```

```
Gly Gly Asp Gly Asp Val Leu Ala Asn Ala Ser Arg Ile His
            915                 920                 925

Tyr Asp Gly Gly Ala Gly Thr Asn Thr Val Ser Tyr Ala Ala Leu Gly
930                 935                 940

Arg Gln Asp Ser Ile Thr Val Ser Ala Asp Gly Glu Arg Phe Asn Val
945                 950                 955                 960

Arg Lys Gln Leu Asn Asn Ala Asn Val Tyr Arg Glu Gly Val Ala Thr
                965                 970                 975

Gln Thr Thr Ala Tyr Gly Lys Arg Thr Glu Asn Val Gln Tyr Arg His
            980                 985                 990

Val Glu Leu Ala Arg Val Gly Gln Val Val Glu Val Asp Thr Leu Glu
995                 1000                1005

His Val Gln His Ile Ile Gly Gly Ala Gly Asn Asp Ser Ile Thr Gly
    1010                1015                1020

Asn Ala His Asp Asn Phe Leu Ala Gly Gly Ser Gly Asp Asp Arg Leu
1025                1030                1035                1040

Asp Gly Gly Ala Gly Asn Asp Thr Leu Val Gly Gly Glu Gly Gln Asn
                1045                1050                1055

Thr Val Ile Gly Gly Ala Gly Asp Asp Val Phe Leu Gln Asp Leu Gly
            1060                1065                1070

Val Trp Ser Asn Gln Leu Asp Gly Gly Ala Gly Val Asp Thr Val Lys
        1075                1080                1085

Tyr Asn Val His Gln Pro Ser Glu Glu Arg Leu Glu Arg Met Gly Asp
    1090                1095                1100

Thr Gly Ile His Ala Asp Leu Gln Lys Gly Thr Val Glu Lys Trp Pro
1105                1110                1115                1120

Ala Leu Asn Leu Phe Ser Val Asp His Val Lys Asn Ile Glu Asn Leu
                1125                1130                1135

His Gly Ser Arg Leu Asn Asp Arg Ile Ala Gly Asp Asp Gln Asp Asn
            1140                1145                1150

Glu Leu Trp Gly His Asp Gly Asn Asp Thr Ile Arg Gly Arg Gly Gly
        1155                1160                1165

Asp Asp Ile Leu Arg Gly Gly Leu Gly Leu Asp Thr Leu Tyr Gly Glu
    1170                1175                1180

Asp Gly Asn Asp Ile Phe Leu Gln Asp Asp Glu Thr Val Ser Asp Asp
1185                1190                1195                1200

Ile Asp Gly Gly Ala Gly Leu Asp Thr Val Asp Tyr Ser Ala Met Ile
                1205                1210                1215

His Pro Gly Arg Ile Val Ala Pro His Glu Tyr Gly Phe Gly Ile Glu
            1220                1225                1230

Ala Asp Leu Ser Arg Glu Trp Val Arg Lys Ala Ser Ala Leu Gly Val
        1235                1240                1245

Asp Tyr Tyr Asp Asn Val Arg Asn Val Glu Asn Val Ile Gly Thr Ser
    1250                1255                1260

Met Lys Asp Val Leu Ile Gly Asp Ala Gln Ala Asn Thr Leu Met Gly
1265                1270                1275                1280

Gln Gly Gly Asp Asp Thr Val Arg Gly Gly Asp Gly Asp Asp Leu Leu
                1285                1290                1295

Phe Gly Gly Asp Gly Asn Asp Met Leu Tyr Gly Asp Ala Gly Asn Asp
            1300                1305                1310

Thr Leu Tyr Gly Gly Leu Gly Asp Asp Thr Leu Glu Gly Gly Ala Gly
        1315                1320                1325

Asn Asp Trp Phe Gly Gln Thr Gln Ala Arg Glu His Asp Val Leu Arg
    1330                1335                1340
```

```
Gly Gly Asp Gly Val Asp Thr Val Asp Tyr Ser Gln Thr Gly Ala His
1345                1350                1355                1360

Ala Gly Ile Ala Ala Gly Arg Ile Gly Leu Gly Ile Leu Ala Asp Leu
            1365                1370                1375

Gly Ala Gly Arg Val Asp Lys Leu Gly Glu Ala Gly Ser Ser Ala Tyr
        1380                1385                1390

Asp Thr Val Ser Gly Ile Glu Asn Val Val Gly Thr Glu Leu Ala Asp
    1395                1400                1405

Arg Ile Thr Gly Asp Ala Gln Ala Asn Val Leu Arg Gly Ala Gly Gly
1410                1415                1420

Ala Asp Val Leu Ala Gly Gly Glu Gly Asp Asp Val Leu Leu Gly Gly
1425                1430                1435                1440

Asp Gly Asp Asp Gln Leu Ser Gly Asp Ala Gly Arg Asp Arg Leu Tyr
            1445                1450                1455

Gly Glu Ala Gly Asp Asp Trp Phe Phe Gln Asp Ala Ala Asn Ala Gly
        1460                1465                1470

Asn Leu Leu Asp Gly Gly Asp Gly Arg Asp Thr Val Asp Phe Ser Gly
    1475                1480                1485

Pro Gly Arg Gly Leu Asp Ala Gly Ala Lys Gly Val Phe Leu Ser Leu
1490                1495                1500

Gly Lys Gly Phe Ala Ser Leu Met Asp Glu Pro Glu Thr Ser Asn Val
1505                1510                1515                1520

Leu Arg Asn Ile Glu Asn Ala Val Gly Ser Ala Arg Asp Asp Val Leu
            1525                1530                1535

Ile Gly Asp Ala Gly Ala Asn Val Leu Asn Gly Leu Ala Gly Asn Asp
        1540                1545                1550

Val Leu Ser Gly Gly Ala Gly Asp Asp Val Leu Leu Gly Asp Glu Gly
    1555                1560                1565

Ser Asp Leu Leu Ser Gly Asp Ala Gly Asn Asp Asp Leu Phe Gly Gly
1570                1575                1580

Gln Gly Asp Asp Thr Tyr Leu Phe Gly Val Gly Tyr Gly His Asp Thr
1585                1590                1595                1600

Ile Tyr Glu Ser Gly Gly Gly His Asp Thr Ile Arg Ile Asn Ala Gly
            1605                1610                1615

Ala Asp Gln Leu Trp Phe Ala Arg Gln Gly Asn Asp Leu Glu Ile Arg
        1620                1625                1630

Ile Leu Gly Thr Asp Asp Ala Leu Thr Val His Asp Trp Tyr Arg Asp
    1635                1640                1645

Ala Asp His Arg Val Glu Ile Ile His Ala Ala Asn Gln Ala Val Asp
1650                1655                1660

Gln Ala Gly Ile Glu Lys Leu Val Glu Ala Met Ala Gln Tyr Pro Asp
1665                1670                1675                1680

Pro Gly Ala Ala Ala Ala Ala Pro Pro Ala Ala Arg Val Pro Asp Thr
            1685                1690                1695

Leu Met Gln Ser Leu Ala Val Asn Trp Arg
        1700                1705

<210> SEQ ID NO 2
<211> LENGTH: 116
<212> TYPE: PRT
<213> ORGANISM: Bordetella pertussis

<400> SEQUENCE: 2

Arg Gly Gly Asp Asp Ile Leu Arg Gly Gly Leu Gly Leu Asp Thr Leu
 1               5                  10                  15
```

```
Tyr Gly Glu Asp Gly Asn Asp Ile Phe Leu Gln Asp Glu Thr Val
             20                  25                  30

Ser Asp Ile Asp Gly Gly Ala Gly Leu Asp Thr Val Asp Tyr Ser
         35                  40                  45

Ala Met Ile His Pro Gly Arg Ile Val Ala Pro His Glu Tyr Gly Phe
 50                  55                  60

Gly Ile Glu Ala Asp Leu Ser Arg Glu Trp Val Arg Lys Ala Ser Ala
 65                  70                  75                  80

Leu Gly Val Asp Tyr Tyr Asp Asn Val Arg Asn Val Glu Asn Val Ile
                 85                  90                  95

Gly Thr Ser Met Lys Asp Val Leu Ile Gly Asp Ala Gln Ala Asn Thr
                100                 105                 110

Leu Met Gly Gln
            115

<210> SEQ ID NO 3
<211> LENGTH: 1705
<212> TYPE: PRT
<213> ORGANISM: Bordetella bronchiseptica

<400> SEQUENCE: 3

Met Gln Gln Ser His Gln Ala Gly Tyr Ala Asn Ala Ala Asp Arg Glu
 1               5                  10                  15

Ser Gly Ile Pro Ala Ala Val Leu Asp Gly Ile Lys Ala Val Ala Lys
                 20                  25                  30

Glu Lys Asn Ala Thr Leu Met Phe Arg Leu Val Asn Pro His Ser Thr
             35                  40                  45

Ser Leu Ile Ala Glu Gly Val Ala Thr Lys Gly Leu Gly Val His Ala
         50                  55                  60

Lys Ser Ser Asp Trp Gly Leu Gln Ala Gly Tyr Ile Pro Val Asn Pro
 65                  70                  75                  80

Asn Leu Ser Lys Leu Phe Gly Arg Ala Pro Glu Val Ile Ala Arg Ala
                 85                  90                  95

Asp Asn Asp Val Asn Ser Ser Leu Ala His Gly His Thr Ala Val Asp
                100                 105                 110

Leu Thr Leu Ser Lys Glu Arg Leu Asp Tyr Leu Arg Gln Ala Gly Leu
            115                 120                 125

Val Thr Gly Met Ala Asp Gly Val Ala Ser Asn His Ala Gly Tyr
        130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Asp Asp Phe Glu Ala Val Lys Val
                165                 170                 175

Ile Gly Asn Ala Ala Gly Ile Pro Leu Thr Ala Asp Ile Asp Met Phe
                180                 185                 190

Ala Ile Met Pro His Leu Ser Asn Phe Arg Asp Ser Ala Arg Ser Ser
            195                 200                 205

Val Thr Ser Gly Asp Ser Val Thr Asp Tyr Leu Ala Arg Thr Arg Arg
        210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270
```

```
Thr Asp Phe Glu Leu Glu Val Arg Asn Ala Leu Asn Arg Arg Ala His
        275                 280                 285
Ala Val Gly Arg Gln Asp Val Gln His Gly Thr Glu Gln Asn Asn
        290                 295                 300
Pro Phe Pro Glu Ala Asp Glu Lys Ile Phe Val Ser Ala Thr Gly
305                 310                 315                 320
Glu Ser Gln Met Leu Thr Arg Gly Gln Leu Lys Glu Tyr Ile Gly Gln
                325                 330                 335
Gln Arg Gly Glu Gly Tyr Val Phe Tyr Glu Asn Arg Ala Tyr Gly Val
                340                 345                 350
Ala Gly Lys Ser Leu Phe Asp Asp Gly Leu Gly Ala Ala Pro Gly Val
                355                 360                 365
Pro Gly Arg Arg Ser Lys Ser Ser Pro Asp Val Leu Glu Thr Val Pro
                370                 375                 380
Ala Ser Pro Gly Leu Arg Arg Pro Ser Leu Gly Ala Val Glu Arg Gln
385                 390                 395                 400
Asp Ser Gly Tyr Asp Ser Leu Asp Gly Val Gly Ser Arg Ser Phe Ser
                405                 410                 415
Leu Gly Glu Val Ser Asp Met Ala Ala Val Glu Ala Ala Glu Leu Glu
                420                 425                 430
Met Thr Arg Gln Val Leu His Ala Gly Ala Arg Gln Asp Asp Ala Glu
                435                 440                 445
Pro Gly Val Ser Gly Ala Ser Ala His Trp Gly Gln Arg Ala Leu Gln
                450                 455                 460
Gly Ala Gln Ala Val Ala Ala Gln Arg Leu Val His Ala Ile Ala
465                 470                 475                 480
Leu Met Thr Gln Phe Gly Arg Ala Gly Ser Thr Asn Thr Pro Gln Glu
                485                 490                 495
Ala Ala Ser Leu Ser Ala Ala Val Phe Gly Leu Gly Glu Ala Ser Ser
                500                 505                 510
Ala Val Ala Glu Thr Val Ser Gly Phe Phe Arg Gly Ser Ser Arg Trp
                515                 520                 525
Ala Gly Gly Phe Gly Val Ala Gly Gly Ala Met Ala Leu Gly Gly Gly
                530                 535                 540
Ile Gly Ala Val Gly Ala Gly Met Ser Leu Thr Asp Asp Ala Pro Ala
545                 550                 555                 560
Gly Gln Lys Ala Ala Ala Gly Ala Glu Ile Ala Leu Gln Leu Thr Gly
                565                 570                 575
Gly Thr Val Glu Leu Ala Ser Ser Ile Ala Leu Ala Leu Ala Ala Ala
                580                 585                 590
Arg Gly Val Thr Ser Gly Leu Gln Val Ala Gly Ala Ser Ala Gly Ala
                595                 600                 605
Ala Ala Gly Ala Leu Ala Ala Leu Ser Pro Met Glu Ile Tyr Gly
                610                 615                 620
Leu Val Gln Gln Ser His Tyr Ala Asp Gln Leu Asp Lys Leu Ala Gln
625                 630                 635                 640
Glu Ser Ser Ala Tyr Gly Tyr Glu Gly Asp Ala Leu Leu Ala Gln Leu
                645                 650                 655
Tyr Arg Asp Lys Thr Ala Ala Glu Gly Ala Val Ala Gly Val Ser Ala
                660                 665                 670
Val Leu Ser Thr Val Gly Ala Ala Val Ser Ile Ala Ala Ala Ala Ser
                675                 680                 685
Val Val Gly Ala Pro Val Ala Val Val Thr Ser Leu Leu Thr Gly Ala
```

```
                690                 695                 700
Leu Asn Gly Ile Leu Arg Gly Val Gln Gln Pro Ile Ile Glu Lys Leu
705                 710                 715                 720

Ala Asn Asp Tyr Ala Arg Lys Ile Asp Glu Leu Gly Gly Pro Gln Ala
                725                 730                 735

Tyr Phe Glu Lys Asn Leu Gln Ala Arg His Glu Gln Leu Ala Asn Ser
                740                 745                 750

Asp Gly Leu Arg Lys Met Leu Ala Asp Leu Gln Ala Gly Trp Asn Ala
                755                 760                 765

Ser Ser Val Ile Gly Val Gln Thr Thr Glu Ile Ser Lys Ser Ala Leu
                770                 775                 780

Glu Leu Ala Ala Ile Thr Gly Asn Ala Asp Asn Leu Lys Ser Ala Asp
785                 790                 795                 800

Val Phe Val Asp Arg Phe Ile Gln Gly Glu Arg Val Ala Gly Gln Pro
                805                 810                 815

Val Val Leu Asp Val Ala Gly Gly Ile Asp Ile Ala Ser Arg Lys
                820                 825                 830

Gly Glu Arg Pro Ala Leu Thr Phe Ile Thr Pro Leu Ala Ala Pro Gly
                835                 840                 845

Glu Glu Gln Arg Arg Arg Thr Lys Thr Gly Lys Ser Glu Phe Thr Thr
850                 855                 860

Phe Val Glu Ile Val Gly Lys Gln Asp Arg Trp Arg Ile Arg Asp Gly
865                 870                 875                 880

Ala Ala Asp Thr Thr Ile Asp Leu Ala Lys Val Val Ser Gln Leu Val
                885                 890                 895

Asp Ala Asn Gly Val Leu Lys His Ser Ile Lys Leu Glu Val Ile Gly
                900                 905                 910

Gly Asp Gly Asp Asp Val Val Leu Ala Asn Ala Ser Arg Ile His Tyr
                915                 920                 925

Asp Gly Gly Ala Gly Thr Asn Thr Val Ser Tyr Ala Ala Leu Gly Arg
                930                 935                 940

Gln Asp Ser Ile Thr Val Ser Ala Asp Gly Glu Arg Phe Asn Val Arg
945                 950                 955                 960

Lys Gln Leu Asn Asn Ala Asn Val Tyr Arg Glu Gly Val Ala Thr Gln
                965                 970                 975

Lys Thr Ala Tyr Gly Lys Arg Thr Glu Asn Val Gln Tyr Arg His Val
                980                 985                 990

Glu Leu Ala Arg Val Gly Gln Leu Val Glu Val Asp Thr Leu Glu His
                995                 1000                1005

Val Gln His Ile Ile Gly Gly Ala Gly Asn Asp Ser Ile Thr Gly Asn
     1010                1015                1020

Ala His Asp Asn Phe Leu Ala Gly Gly Ala Gly Asp Arg Leu Asp
1025                1030                1035                1040

Gly Gly Ala Gly Asn Asp Thr Leu Val Gly Gly Glu Gly His Asn Thr
                1045                1050                1055

Val Val Gly Gly Ala Gly Asp Asp Val Phe Leu Gln Asp Leu Gly Val
          1060                1065                1070

Trp Ser Asn Gln Leu Asp Gly Gly Ala Gly Val Asp Thr Val Lys Tyr
          1075                1080                1085

Asn Val His Gln Pro Ser Glu Glu Arg Leu Glu Arg Met Gly Asp Thr
     1090                1095                1100

Gly Ile His Ala Asp Leu Gln Lys Gly Thr Val Glu Lys Trp Pro Ala
1105                1110                1115                1120
```

```
Leu Asn Leu Phe Ser Val Asp His Val Lys Asn Ile Glu Asn Leu His
            1125                1130                1135

Gly Ser Ser Leu Asn Asp Ser Ile Ala Gly Asp Arg Asp Asn Glu
            1140                1145                1150

Leu Trp Gly Asp Asp Gly Asn Asp Thr Ile His Gly Arg Gly Gly Asp
        1155                1160                1165

Asp Ile Leu Arg Gly Gly Leu Gly Leu Asp Thr Leu Tyr Gly Glu Asp
    1170                1175                1180

Gly Asn Asp Ile Phe Leu Gln Asp Asp Glu Thr Val Ser Asp Asp Ile
1185                1190                1195                1200

Asp Gly Gly Ala Gly Leu Asp Thr Val Asp Tyr Ser Ala Met Ile His
            1205                1210                1215

Ala Gly Lys Ile Val Ala Pro His Glu Tyr Gly Phe Gly Ile Glu Ala
            1220                1225                1230

Asp Leu Ser Glu Gly Trp Val Arg Lys Ala Ala Arg Arg Gly Met Asp
            1235                1240                1245

Tyr Tyr Asp Ser Val Arg Ser Val Glu Asn Val Ile Gly Thr Ser Met
        1250                1255                1260

Lys Asp Val Leu Ile Gly Asp Ala Gln Ala Asn Thr Leu Met Gly Gln
1265                1270                1275                1280

Gly Gly Asp Asp Thr Val Arg Gly Gly Asp Gly Asp Asp Leu Leu Phe
            1285                1290                1295

Gly Gly Asp Gly Asn Asp Met Leu Tyr Gly Asp Ala Gly Asn Asp Thr
        1300                1305                1310

Leu Tyr Gly Gly Leu Gly Asp Asp Thr Leu Glu Gly Gly Ala Gly Asn
    1315                1320                1325

Asp Trp Phe Gly Gln Thr Pro Ala Arg Glu His Asp Val Leu Arg Gly
    1330                1335                1340

Gly Ala Gly Val Asp Thr Val Asp Tyr Ser Gln Ala Gly Ala His Ala
1345                1350                1355                1360

Gly Val Ala Thr Gly Arg Ile Gly Leu Gly Ile Leu Ala Asp Leu Gly
            1365                1370                1375

Ala Gly Arg Val Asp Lys Leu Gly Glu Ala Gly Ser Ser Ala Tyr Asp
            1380                1385                1390

Thr Val Ser Gly Ile Glu Asn Val Val Gly Thr Glu Leu Ala Asp Arg
        1395                1400                1405

Ile Thr Gly Asp Ala Gln Ala Asn Val Leu Arg Gly Ala Gly Gly Ala
    1410                1415                1420

Asp Val Leu Ala Gly Gly Glu Gly Asp Asp Val Leu Leu Gly Gly Asp
1425                1430                1435                1440

Gly Asp Asp Gln Leu Ser Gly Asp Ala Gly Arg Asp Arg Leu Tyr Gly
            1445                1450                1455

Glu Ala Gly Asp Asp Trp Phe Phe Gln Asp Ala Ala Asn Ala Gly Asn
            1460                1465                1470

Leu Leu Asp Gly Gly Asp Gly Asn Asp Thr Val Asp Phe Ser Gly Pro
        1475                1480                1485

Gly Arg Gly Leu Asp Ala Gly Ala Lys Gly Val Phe Leu Ser Leu Gly
    1490                1495                1500

Lys Gly Phe Ala Ser Leu Met Asp Glu Pro Glu Thr Ser Asn Val Leu
1505                1510                1515                1520

Arg His Ile Glu Asn Ala Val Gly Ser Val Arg Asp Asp Val Leu Ile
            1525                1530                1535

Gly Asp Ala Gly Ala Asn Val Leu Asn Gly Leu Ala Gly Asn Asp Val
            1540                1545                1550
```

```
Leu Ser Gly Gly Ala Gly Asp Asp Val Leu Gly Asp Glu Gly Ser
        1555                1560                1565

Asp Leu Leu Ser Gly Asp Ala Gly Asn Asp Asp Leu Phe Gly Gly Gln
    1570                1575                1580

Gly Asp Asp Thr Tyr Leu Phe Gly Ala Gly Tyr Gly His Asp Thr Ile
1585                1590                1595                1600

Tyr Glu Ser Gly Gly Gly His Asp Thr Ile Arg Ile Asn Ala Gly Ala
            1605                1610                1615

Asp Gln Leu Trp Phe Ala Arg Gln Gly Asn Asp Leu Glu Ile Arg Ile
        1620                1625                1630

Leu Gly Thr Asp Asp Ala Leu Thr Val His Asp Trp Tyr Arg Asp Ala
    1635                1640                1645

Asp His Arg Val Glu Ala Ile His Ala Ala Asn Gln Ala Ile Asp Pro
1650                1655                1660

Ala Gly Ile Glu Lys Leu Val Glu Ala Met Ala Gln Tyr Pro Asp Pro
1665                1670                1675                1680

Gly Ala Ala Ala Ala Ala Pro Pro Ala Ala Arg Val Pro Asp Thr Leu
            1685                1690                1695

Met Gln Ser Leu Ala Val Asn Trp Arg
        1700                1705

<210> SEQ ID NO 4
<211> LENGTH: 116
<212> TYPE: PRT
<213> ORGANISM: Bordetella bronchiseptica

<400> SEQUENCE: 4

Arg Gly Gly Asp Asp Ile Leu Arg Gly Gly Leu Gly Leu Asp Thr Leu
1               5                   10                  15

Tyr Gly Glu Asp Gly Asn Asp Ile Phe Leu Gln Asp Asp Glu Thr Val
            20                  25                  30

Ser Asp Asp Ile Asp Gly Gly Ala Gly Leu Asp Thr Val Asp Tyr Ser
        35                  40                  45

Ala Met Ile His Ala Gly Lys Ile Val Ala Pro His Glu Tyr Gly Phe
    50                  55                  60

Gly Ile Glu Ala Asp Leu Ser Glu Gly Trp Val Arg Lys Ala Ala Arg
65                  70                  75                  80

Arg Gly Met Asp Tyr Tyr Asp Ser Val Arg Ser Val Glu Asn Val Ile
                85                  90                  95

Gly Thr Ser Met Lys Asp Val Leu Ile Gly Asp Ala Gln Ala Asn Thr
            100                 105                 110

Leu Met Gly Gln
        115

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 5
gtactgatta taaagatgac gatgacaaat cac                                  33

<210> SEQ ID NO 6
<211> LENGTH: 33
<212> TYPE: DNA
```

```
<213> ORGANISM: Artificial Sequence
<220> FEATURE:
<223> OTHER INFORMATION: Description of Artificial Sequence:
      Synthetic primer

<400> SEQUENCE: 6
gtacgtgatt tgtcatcgtc atctttataa tca                                 33

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 7
gtacttatcg attataaaga tgacgatgac aaa                                 33

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 8
gtactttgtc atcgtcatct ttataatcga taa                                 33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 9
gtacgtggat tataaagatg acgatgacaa agc                                 33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 10
gtacgctttg tcatcgtcat ctttataatc cac                                 33

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 11

Asp Tyr Lys Asp Asp Asp Asp Lys
  1               5

<210> SEQ ID NO 12
<211> LENGTH: 5
<212> TYPE: PRT
<213> ORGANISM: Artificial Sequence
```

-continued

```
<220> FEATURE:
<223> OTHER INFORMATION: Description of Artificial Sequence:
      Synthetic peptide

<400> SEQUENCE: 12

Met Gly Cys Gly Asn
 1               5
```

MODIFIED *BORDETELLA* ADENYLATE CYCLASE COMPRISING OR LACKING CD11B/CD18 INTERACTION DOMAIN AND USES THEREOF

CROSS REFERENCE TO RELATED APPLICATIONS

This application is a Continuation of U.S. application Ser. No. 11/304,590, filed Dec. 16, 2005 (now abandoned), which is a Continuation of PCT International Application No. PCT/EP2004/007811, filed on Jun. 18, 2004, which claimed the priority of European Patent Application No. 03291486.3, filed Jun. 18, 2003, the contents of each are incorporated herein by reference.

The invention relates to modified *Bordetella* adenylate cyclase toxins which are deficient for CD11b/CD18 binding and to their use in the preparation of pharmaceutical composition for the treatment of whooping cough and/or for the protection against *Bordetella* infection. The invention also relates to specific fragments of *Bordetella* adenylate cyclase comprising the CD11b/CD18 interaction domain and to their use, especially for targeting a molecule of interest to CD11b expressing cells.

The genus *Bordetella* comprises four species, i.e., *Bordetella pertussis, Bordetella parapertussis, Bordetella bronchiseptica* and *Bordetella avium*.

The bordetellae are Gram-negative coccobacilli responsible for respiratory infections. *Bordetella pertussis* and *Bordetella parapertussis* are strictly human pathogens. *Bordetella bronchiseptica* is pathogenic for various mammals, and more rarely for man, and, in distinction to *B. pertussis* and *B. parapertussis*, is capable of surviving outside the host. *Bordetella avium* is pathogenic for birds.

The most virulent species to man is *B. pertussis*, which is the etiologic agent of whooping cough, a highly contagious childhood respiratory disease, characterized by bronchopneumonia and paroxysmal coughing interrupted by inspiratory whoops.

The vaccination against whooping cough has hitherto been most usually carried out with the aid of inactivated whole bacteria. However, such vaccines are not always devoid of toxicity in view of the fact that the virulence factors are constituted by proteins secreted by the bacteria and not by the bacteria themselves. The proteins can thus exert serious pathological effects, even after the death of the bacteria.

European patent EP 0 424 518 (Institut Pasteur) recites the use of *Bordetella* adenylate cyclase as protective antigens against both *Bordetella pertussis* and *Bordetella bronchiseptica*.

European patent EP 0 338 169 (Institut Pasteur) also describes the use of active adenylate cyclase preparations from *Bordetella parapertussis* as protective antigens against whooping cough.

Alternate strategies have also been developed, including the preparation of acellular vaccine using immunogenic detoxified toxins of *Bordetella*.

An example of a vaccine based on detoxified pertussis toxin is described in U.S. Pat. No. 6,040,427 (Locht et al., 2000).

Among the variety of toxins produced by *B. pertussis*, the adenylate cyclase (also referred hereafter by the term CyaA) is a crucial factor in the virulence strategy of the bacteria during the early phases of respiratory tract colonization (Goodwin and Weiss, 1990; Khelef et al., 1992). The toxin allows the pathogen to escape host immune surveillance, mainly, by intoxicating neutrophils and macrophages causing phagocyte impotence and inducing macrophage apoptosis (Confer and Eaton, 1982; Gueirard et al., 1998; Harvill et al., 1999; Khelef and Guiso, 1995; Khelef et al., 1993). The role of CyaA in the pathogenesis of *B. pertussis* was clearly demonstrated in mouse respiratory model. Indeed, genetically modified *B. pertussis* strains deficient for the expression of CyaA were impaired in their ability to induce pulmonary lesions and to cause lethal infection (Khelef et al., 1994; Weiss and Goodwin, 1989). On the other hand, CyaA was shown to induce protective immunity against *B. pertussis* lung colonization in a mouse model Betsou et al., "CyaC-mediated activation is important not only for toxic but also for protective activities of *Bordetella pertussis* adenylate cyclase hemolysin," *Infect. Immure.*, (1993) 61:3583-3589; and Betsou et al., "The C-terminal domain is essential for protective activity of the *Bordetella pertussis* adenylate cyclase hemolysin," *Infect. Immun.* (1995) 63:3309-3315, and Hormozi et al, "Adjuvant and protective properties of native and recombinant *Bordetella pertussis* adenylate cyclase toxin preparations in mice," *FEMS Immunol Med Microbiol*, (1999) 23, 273-282.

CyaA is a 1706 amino acid residue-long polypeptide consisting of four functional domains; the adenylate cyclase activity (AC) domain (residues 1 to 400), the hydrophobic channel-forming domain (residues 500 to 700), the calcium-binding glycin/aspartate rich repeat domain (residues 1000 to 1600), and the C-terminal domain harboring a secretion signal (residues 1600 to 1706). CyaA is able to invade eukaryotic cells and translocate its catalytic domain into the cytoplasm where, upon activation by endogenous calmodulin, it catalyzes the conversion of ATP into cAMP (Ladant and Ullmann, 1999). The accumulation of cAMP in the cell cytosol is considered to be responsible for the toxic effect of this toxin (Rogel et al., 1991). The main consequences of this intoxication are cell apoptosis and the alteration of phagocytic abilities and superoxide production (Confer and Eaton, 1982; Friedman et al., 1987; Khelef et al., 1993; Njamkepo et al., 2000; Pearson et al., 1987).

The whole sequence of *Bordetella pertussis* adenylate cyclase is shown in SEQ ID NO: 1.

The whole sequence of *Bordetella bronchiseptica* adenylate cyclase is shown in SEQ ID NO: 3.

CyaA requires calcium to acquire a translocation-specific conformation that allows the delivery of the catalytic domain into the cell cytosol (Rogel and Hanski, 1992; Rose of al., 1995). Primarily, CyaA is produced as an inactive protoxin, proCyaA, which after post-translational modification by an acyltransferase, the product of the cyaC gene, becomes an active toxin. This covalent post-translational fatty-acylation is required for translocation of the toxin through target cell membranes and the delivery of its catalytic AC domain as well as for the formation of hemolytic cation-selective channels. Acylation of proCyaA occurs at two different positions, Lys-983 and Lys-860, which are located within conserved RTX acylation sites (Barry et al., 1991; Hackett et al., 1994). While acylation of Lys-860 seems not to be necessary for CyaA activity, acylation of Lys-983 has been shown to be crucial (Basar of al., 2001).

CyaA can penetrate a wide range of cell types, including the mammalian erythrocytes lacking membrane trafficking (Bellalou et al., 1990; Gray et al., 1999; Rogel and Hanski, 1992). In contrast, CyaA toxicity effects such as the abrogation of phagocytic capacity and the induction of apoptosis were mainly elucidated on immune cells, namely neutrophils and macrophages (Confer and Eaton, 1982; Khelef et al., 1993). In addition, in a mouse respiratory infection, CyaA was shown to display specific intoxication towards alveolar macrophages (Gueirard et al., 1998). Vaccine comprising recombinant adenylate cyclase toxin produced by *B. pertussis* fixed to heterologous epitopes is also described in patent WO 93/21324 (Institut Pasteur, 1993). It has been recently demonstrated that CyaA binds specifically to target cells through the $\alpha_M\beta_2$ integrin (CD11b/CD18). This binding was saturable and completely inhibited by anti-CD11b monoclonal antibodies. CyaA displayed a selective cytotoxicity towards CD11b+ cells showing that its interaction with CD11b is required for the translocation of the catalytic domain and the subsequent cAMP increase and cell death. Moreover, sensitivity of CHO cells to CyaA cytotoxicity was dramatically increased upon expression of the CD11b/CD18 heterodimer. Furthermore, $Ca^{2+}$ ions that are required for the catalytic domain translocation into cells were also strictly necessary for CyaA interaction with CD11b (Guermonprez et al., 2001). The importance of CD11b for interaction of CyaA with cells was further demonstrated in a system where CyaA is used as a vector to deliver foreign antigens into antigen presenting cells, such as dendritic cells. Only dendritic cells of the CD11c+CD8α-CD11b$^{high}$ subset were, indeed, able to display MHC class I peptide complexes corresponding to the epitope inserted in the recombinant CyaA (Guermonprez et al., 2002).

The CD11b protein is a member of the large family of $\beta_2$ integrins, the leukocyte adhesion molecules, which comprizes LFA1 (CD11a), MAC-1 (CD11b) and p150,95 (CD11c). The members of this family differ by their α-chain which is expressed as an obligate heterodimer with a β chain (CD18) (Arnaout, 1990). CD11b, also known as complement type 3 receptor (CR3), is expressed on macrophages, neutrophils, dendritic cells, NK cells, peritoneal B-1 cells and a subset of CD8+ T cells (Arnaout, 1990; Bell et al., 1999). It plays a key role in leukocyte adhesive functions and triggers phagocytosis of complement coated particles (Diamond and Springer, 1993). CD11b binds various ligands, such as the intracellular adhesion molecule ICAM-1, fibrinogen, coagulant factor X and inactivated complement component C3b (iC3b) (Altieri and Edgington, 1988; Beller et al., 1982; Diamond et al., 1990; Wright et al., 1988).

Based on the binding properties of CyaA to CD11b/CD18, European patent application EP1188446 (Institut Pasteur) describes proteinaceous vectors comprising recombinant *Bordetella* species adenylate cyclase for targeting a molecule of interest, and especially an antigen to dendritic cells.

The present invention is now based on the discovery that one or several regions of the *Bordetella pertussis* adenylate cyclase comprised within the amino acid sequence extending from amino acid 1166 to amino acid 1281 (SEQ ID NO:2) are critical for the interaction of the toxin with CD11b/CD18. This region, necessary to provide binding capacity of CyaA to CD11b/CD18 can further be combined with other regions of CyaA acting as accessory regions.

This discovery affords the opportunity to prepare an efficient and versatile molecule delivery vector capable of targeting a molecule of interest to dendritic cells. Alternatively, the deletion of the identified CD11b/CD18 interaction domain of adenylate cyclase can be used advantageously to design a safe a cellular vaccine for the protection against *Bordetella* infection, and especially, *Bordetella pertussis* infection.

The invention also provides the use of the identified CD11b/CD18 interaction domain to generate neutralizing antibodies, capable of blocking the interaction of native adenylate cyclase produced by infectious bacteria with cell receptors.

It is thus an object of this invention to provide a protein consisting of a *Bordetella* adenylate cyclase which is modified in the CD11b/CD18 interaction domain by one or more amino acid deletion, substitution, or insertion, wherein said protein is deficient for CD11b/CD18 binding but is specifically reactive with antisera recognizing a wild-type *Bordetella* adenylate cyclase.

The protein of the invention can be used, as the active principle, in a vaccine against whooping cough. The mutation(s) within the CD11b/CD18 interaction domain thus preserves immune cells from potentially negative effects, such as signalling upon the integrin engagement by the toxoid and/or some functional interference due to competition for binding to CD11b with the CyaA toxoid, which also serves as the complement receptor CR3.

As used herein, the term "polypeptide" refers to a single chain of amino acids linked by peptide bonds, comprising at least 6 amino acids, preferably at least 10 amino acids, and more preferably at least 50 amino acids.

The term "protein" refers to a macromolecule which essentially consists of one or more polypeptides.

The term "*Bordetella* adenylate cyclase" encompasses, within the present invention, the calmodulin-dependent adenylate cyclase which is naturally synthesized in *Bordetella* species, and which is a major virulence factor mandatory for the initial phases of bacterial colonization in the lung.

In one preferred embodiment, the protein of the invention is obtained by modification of the *Bordetella pertussis* adenylate cyclase, the agent of whooping cough in human.

In *Bordetella pertussis*, the adenylate cyclase is synthesized and secreted in the form of a polypeptide of 1706 amino acids (SEQ ID NO:1): The calmodulin-dependent catalytic activity is localized in the first 400 amino acids, this domain being hereafter referred to as "the N-terminal catalytic domain". As previously reported, in order to be active, said adenylate cyclase toxin is rendered invasive and hemolytic when post-translationally modified by the coexpression of the cyaC gene product.

According to the present invention, the expression "CD11b/CD18 interaction domain" refers either to a. the CD11b/CD18 interaction domain of *Bordetella pertussis* extending from amino acid 1166 to amino acid 1281 of *Bordetella pertussis* adenylate cyclase (SEQ ID NO:2), or b. the domain of the adenylate cyclase of a *Bordetella* species corresponding to the CD11b/CD18 interaction domain of *Bordertella pertussis*, as identified by aligning the sequence of the adenylate cyclase of said *Bordetella* species with the sequence of adenylate cyclase of *Bordetella pertussis* using an algorithm for searching best local alignment.

An example of an algorithm for searching best local alignment is the BLAST algorithm (Altschul et al., 1990).

The CD11b/CD18 interaction domain of *Bordetella bronchiseptica* is represented by SEQ ID NO: 4.

As used herein, the expression "deficient for CD11b/CD18 binding" means that the protein of the invention does not compete with the wild-type *Bordetella* adenylate cyclase for binding to CD11b/CD18 $\alpha_m\beta_2$ expressing cells. The "CD11b/CD18 $\alpha_m\beta_2$" or "CD11b/CD18" refers to the cellular receptor of the *Bordetella* adenylate cyclase (Guermonprez et al., 2001). Examples of binding assays to evaluate specific binding of a recombinant toxin to CD11b/CD18 $\alpha_m\beta_2$ expressing cells are described in the following experimental part. The protein of the invention preferably has less than 50% of binding affinity to CD11b/CD18 $\alpha_m\beta_2$ as compared to wild-type *Bordetella* adenylate cyclase. Most preferably, the protein of the invention has less than 10% and more preferably less than 5% of the assayed binding affinity.

As used hereafter, the term "CD11b expressing cells" relates to the cells that express the CD11b/CD18 $\alpha_m\beta_2$ on their surface. In particular, these cells are granulocytes/neutrophils, macrophages, NK cells, subsets of T CD8+ and B cells and myeloid dendritic cells.

To provide the protein of the invention, the CD11b/CD18 interaction domain of a *Bordetella* adenylate cyclase is modified by insertion, deletion or substitution of one or more amino acid, the resulting protein being deficient for CD11b/CD18 binding.

In one embodiment of the invention, the CD11b/CD18 interaction domain is modified by insertion of a peptide therein. For example, a sequence consisting of between 6 to 12 residues is inserted in the CD11b/CD18 interaction domain.

Specific embodiments include *Bordetella pertussis* adenylate cyclase modified by insertion between residues 1166 and 1167 or between residues 1281 and 1282 (the number indicates the position of the amino acids in the wild type *Bordetella pertussis* adenylate cyclase), of a peptide containing between 6 to 12 amino acids. Examples of epitope insertions of the FLAG sequence at these positions are described in the following Experimental Part, hereafter referred to as CyaA1166/FLAG and CyaA1281/FLAG.

Alternatively, the residues which are shown to be involved in the binding to CD11b/CD18 can be deleted or replaced by non-functional residues.

In one specific embodiment, the *Bordetella* adenylate cyclase is modified by insertion, deletion or substitution of one or more amino acid in the region extending from residue 1208 to 1243 in *Bordetella pertussis* adenylate cyclase or in corresponding regions of other *Bordetella* adenylate cyclases.

Preferred embodiments of the protein of the invention include a *Bordetella pertussis* adenylate cyclase containing deletions of one or more of the amino acids or their replacement by non-functional amino acids.

In one preferred embodiment, the *Bordetella* adenylate cyclase is modified by the complete deletion of the CD11b/CD18 interaction domain.

According to another specific embodiment of the invention, the *Bordetella pertussis* adenylate cyclase is modified by deletion of the amino acids extending from position 1245 to position 1273, these amino acids being optionally replaced by non functional amino acids, for example an octapeptide as exemplified in the Experimental Part, hereafter referred to as the CyaAΔ1245-1273.

Additionally, to ensure complete safety of the administration in living organism of the protein of the invention, the *Bordetella* adenylate cyclase is modified such that the catalytic activity is ablated. According to one embodiment of the invention, the *Bordetella* adenylate cyclase is further modified by insertion, deletion or substitution of one or more amino acids in the N-terminal catalytic domain, wherein said modified *Bordetella* adenylate cyclase has a catalytic activity which is decreased as compared to the wild-type *Bordetella* adenylate cyclase catalytic activity. Preferably, the catalytic activity represents less than 10% of the catalytic activity of the wild-type *Bordetella* adenylate cyclase and is more preferably non significant.

Examples of mutants in the N-terminal catalytic domain are described in the Art (for example in WO 93/21324, Institut Pasteur).

Embodiments of the protein of the invention include modified *Bordetella* species adenylate cyclase lacking at least the amino acids 1 to 300 of the N-terminal catalytic domain and preferably lacking amino acids 1 to 373.

Alternatively, dipeptide insertions can be done into the ATP-binding site between residues 188 and 190 of adenylate cyclase of *Bordetella pertussis*, or the corresponding residues in adenylate cyclase from other *Bordetella* species.

It is also shown in the present invention that acylation of the *Bordetella* adenylate cyclase is involved in CD11b/CD18 binding and subsequent translocation of the toxin into the cell. Accordingly, in one preferred embodiment of the protein of the invention, the protein is not acylated. Especially, the *Bordetella* adenylate cyclase is further modified in the amino acids which are acylated post-translationally. These amino acids correspond to Lys-983 and Lys-860 of the *Bordetella pertussis* adenylate cyclase.

In this particular embodiment, the protein is not acylated in position 983 and/or 860 of the adenylate cyclase sequence.

In another embodiment, the protein of the invention is acylated.

The protein of the invention is preferably immunogenic, yet substantially non toxic protein, i.e. a protein that is at least deficient for cell receptor binding, and optionally in adenylate cyclase activity, but which is still specifically recognized by anti-adenylate cyclase toxin antibodies.

The invention also relates to the pharmaceutical composition comprising the protein defined above, in combination with a pharmaceutically acceptable vehicle.

According to one embodiment, said composition is a vaccine suitable for administration in a human or an animal. The vaccine is preferably capable of inducing immunity against whooping cough. Such vaccine comprises an immunoprotective and non-toxic amount of the protein of the invention. Said composition may further comprise one or several suitable priming adjuvants accordingly. Other antigens which are known to be desirably administered in conjugation with the protein of the invention may also be included in the vaccine of the invention. Such additional components include other known protective antigens of *Bordetella*, tetanus toxoid and/or diphteria toxoid.

Naturally, the invention further relates to a method for immunizing a human or an animal against *Bordetella* infection and/or symptoms associated to disease caused by *Bordetella* infection, which comprises administering the vaccine of the subject invention to such human or animal.

The route of administration of the vaccine of the invention may be any suitable route which delivers an immunoprotective amount of the protein of the invention to the host. However, the vaccine is preferably administered parenterally via the intramuscular or subcutaneous routes. Other routes of administration may also be employed, where desired, such as oral administration or via other parenteral routes, i.e., intradermally, intranasally or intravenously.

Another aspect of the present invention relates to the use of the protein of the invention, in the preparation of a medicament for the treatment, in human or in an animal, of disease symptoms associated with whooping cough and/or for protecting a human or an animal against the disease symptoms associated with *Bordetella* infection.

Naturally, the invention further relates to a method for treating a human or an animal against *Bordetella* infection and/or symptoms associated to disease caused by *Bordetella* infection, which comprises administering the medicament of the subject invention to such human or animal.

Another aspect of the invention is a polypeptide capable of binding to CD11b/CD18 integrin, said polypeptide being either a. a fragment of a *Bordetella* adenylate cyclase having between 30 to 500 amino acids, preferably between 50 to 300, and more preferably between 50 to 150 amino acids, said fragment comprising the CD11b/CD18 interaction domain of said *Bordetella* adenylate cyclase, or comprising a fragment of said wild type CD11b/CD18 interaction domain sufficient to retain the capacity to bind to CD11b/CD18, or, b. a variant of said fragment having at least 70% identity preferably at least 80% identity and more preferably at least 90% identity with said fragment, wherein said variant retains the capability to bind to CD11b/CD18.

The *Bordetella* adenylate cyclase is preferably selected among *Bordetella pertussis, Bordetella parapertussis* and *Bordetella bronchiseptica*, and more preferably *Bordetella pertussis*.

The polypeptides of the invention will be selected among those which adopt an appropriate conformation to bind to the CD11b/CD18.

In specific embodiments, the polypeptides of the invention may comprise other accessory regions of the *Bordetella* adenylate cyclase, which are involved in optimal binding to CD11b/CD18. The regions include more specifically, amino acid sequences comprised in the region extending from 1416 to 1648.

In one preferred embodiment, the polypeptide of the invention is a variant as defined above in b., consisting of one or more fragments from 10 to 50 amino acids of the CD11b/CD18 interaction domain. For example, in one preferred embodiment, said polypeptide comprises at least fragments from 10 to 50 amino acids of the region of *B. pertussis* adenylate extending from amino acid 1208 to amino acid 1243 of *B. pertussis* adenylate cyclase.

Percentage identity corresponds to the percentage of amino acids of the variant sequence which are identical to the wild-type sequence when both sequences are aligned using the BLAST algorithm. The expression "retains the capacity to bind to CD11b/CD18" means that the variant retains at least 80% of the binding affinity to CD11b/CD18 as compared to the wild-type corresponding fragment from which it can be aligned, and preferably, at least 90% of the binding affinity to CD11b/CD18.

According to one preferred embodiment, said polypeptide is specifically reactive with antisera recognizing *Bordetella* wild-type adenylate cyclase, preferably *Bordetella pertussis* adenylate cyclase. More preferably, said polypeptide is capable, when administered to a mammal, of raising antibodies recognizing specifically *Bordetella* adenylate cyclase.

In one specific embodiment, said polypeptide is a fragment of the *Bordetella pertussis* adenylate cyclase. In another specific embodiment, is said polypeptide essentially consists of the CD11b/CD18 interaction domain, and more specifically to CD11b/CD18 interaction domain of *B. pertussis*, extending from amino acid 1166 to amino acid 1281 of *B. pertussis* adenylate cyclase (SEQ ID NO:2).

In other specific embodiments, said polypeptide further comprises an acylation domain of the *Bordetella* adenylate cyclase and/or the hydrophobic domain. Said acylation domains are included in the corresponding regions extending from residue 700 to residue 1000 of SEQ ID NO: 1, as described in WO 93/21324 and comprise Lys 983 and/or Lys 860. The hydrophobic domain corresponds to the region extending from residue 500 to residue 700 of SEQ ID NO: 1.

Preferably, said polypeptide is not toxic when administered in vivo to a mammal.

The polypeptides of the invention compete for the binding of the CD11b/CD18 integrin with wild-type adenylate cyclase.

The invention thus relates to the use of the polypeptide as defined above, in the preparation of a vaccine or a medicament for the prevention or treatment, in human or in an animal, of disease symptoms associated with whooping cough and/or for protecting a human or an animal against the disease associated with *Bordetella* infection.

More specifically, the invention concerns the use of said polypeptide of the invention to generate protective antibodies against *Bordetella* infection.

It has already been reported that adenylate cyclase is an efficient molecule delivery vector capable of targeting different antigens to dendritic cells leading especially to the generation of potent CD4+ as well as CD8+ T cell responses (EP1188446, Institut Pasteur).

The present invention now relates to the use of the polypeptides of the invention, in the preparation of a vector for targeting a molecule of interest, specifically to CD11b expressing cells.

The term "specifically" means within the context of the present invention that the polypeptide when used as a vector for a molecule of interest, is directed preferentially to CD11b expressing cells according to the high binding affinity of the CD11b/CD18 interaction domain with the CD11b/CD18, thereby offering means to target the molecule of interest at the surface of said cells or within said cells in a selective way with respect to other cells.

In particular, in one embodiment, the targeting of said molecule or peptide is effective in vivo. In other embodiments, the targeting of said molecule is effective in vitro or ex vivo. By "in vitro", it is meant that the target cells are cells, which are cultured in vitro. By "ex vivo", it is meant that the target cells are cells, which have been extracted from a living organism, are cultured in vitro and are intended to be readministered in a living organism.

The invention thereby provides means appropriate for the design of compositions suitable for administration to animal or human hosts requiring targeting of certain leukocytes and in particular myeloid dendritic cells, neutrophils or macrophages.

The invention more specifically relates to a vector for targeting a molecule of interest to CD11b expressing cells, characterized in that said vector comprises the polypeptide capable of binding to CD11b/CD18, as defined above, coupled to said molecule of interest.

The invention also relates to a method for in vitro targeting a molecule of interest to CD11b expressing cells, said method comprising:

a. providing CD11b expressing cells extracted from a living organism, b. culturing said CD11b expressing cells with the vector of the invention under appropriate conditions for targeting said vector to said CD11b expressing cells.

The invention also provides CD11b-expressing cells comprising a molecule of interest as obtainable by the above-defined method.

According to the present invention, the expression "molecule of interest" refers to any molecule, preferably a molecule which is not a fragment of a *Bordetella* species adenylate cyclase.

The molecules of interest can also be selected among the nucleic acids, such as DNA, RNA, oligonucleotides, antisense DNA, plasmids and cosmids. They can also be selected among the peptides or polypeptides, and especially, the enzymes, co-enzymes, receptor ligands, haptens, antigens, antibodies and fragments thereof. Naturally, the person skilled in the Art will select the appropriate molecule depending upon the desired use.

Molecules of interest can be selected among the active principle of the medicament, the immunotoxins, the antioxidants, the antibiotics, the growth factors, the intracellular hormones, the cytokines, the toxins, the neuromediators, the antimicrobial agents, especially, antiviral, antibacterial, antiparasital or antitumoral and more generally, any therapeutical or prophylactic agent of interest.

According to one specific embodiment, a molecule of interest is selected among the group consisting of: peptides, glycopeptides, lipopeptides, polysaccharides, oligosaccharides, nucleic acids, lipids and chemicals.

In specific embodiments, a molecule of interest is a heterologous antigen or epitope, the term "heterologous" referring to an antigen or epitope other than the adenylate cyclase antigenic determinant comprised in the vector itself.

The molecule of interest is coupled to the polypeptide of the invention to provide the vector of the invention.

As used herein, the term "coupled" means any interaction allowing physical association of the molecule of interest and the polypeptide. Preferably, the coupling is covalent. It can be direct covalent coupling or indirect coupling by the use of a linkage agent to form a conjugate. Chemical linkage methods are well known in the Art. Chemical linkage can be selected for example among maleimide, peptidic, disulfide or thioether linkage. For example, disulfide linkage using N-pyridyl sulfonyl-activated sulfhydryl can be used.

One specific method consists in adding a linker to the polypeptide, said linker consisting of at least one cysteine which can be easily used for disulfide linkage. Another approach consists of coupling chemically a biotinyl moiety, which enables the coupling of other molecules associated to streptavidin.

Multiple molecules can be chemically coupled to the polypeptide of the invention by means of a disulfide bond to different cysteine residues, provided that the coupling does not prevent interaction with the CD11b/CD18.

The functional properties of the CD11b expressing cells define furthermore a use of said polypeptides of the invention in the manufacturing of a proteinaceous vector for drug targeting to these specific cells. In this context, in one specific embodiment of the invention, the so-called molecule of interest is an active principle of a medicament. Said active principle may be chemically or genetically coupled to the polypeptide of the invention. Advantageously, a molecule of interest is an anti-inflammatory drug which is, when coupled to the adenylate cyclase toxin, specifically targeted to the surface of the cells involved of the inflammatory response, such as neutrophils.

Since CD11b expressing cells and more specifically the myeloid dendritic cells, the neutrophils and the macrophages are involved in essential functions of the immune and innate defence system, in particular in inflammatory and specific immune responses, in a preferred embodiment of the invention, the vector of the invention is more specifically designed to prime CD4+ and CD8+ cells response, said response following the targeting of the molecule of interest to CD11b expressing cells, in particular myeloid dendritic cells.

In this context, the molecule of interest is or comprises preferably an epitope or an antigen. More specifically, the molecule of interest can be especially an antigen selected from the group consisting of: a poliovirus antigen, an HIV virus antigen, an influenza virus antigen, a lymphocytic choromeningitidis virus, eptitope, a human papillomavirus (HPV) antigen, a bacterial antigen, a *mycobacterium tuberculosis* antigen for instance.

The invention thus provides means to prime CD4+ and CD8+ cells response in a patient, either by in vivo targeting antigen or epitope to CD11b expressing cells or by ex vivo targeting antigen or epitope to extracted CD11b expressing cells and re-administering the resulting cells to said patient.

Accordingly, the invention relates to a method for in vitro targeting an antigen or an epitope to CD11b expressing cells, said method comprising a. providing CD11b expressing cells extracted from a living organism, and,
b. culturing said CD11b expressing cells with the vector of the invention carrying an antigen or an epitope as a molecule of interest under appropriate conditions for targeting the vector to said CD11b expressing cells.

Preferably, CD11b-expressing cells extracted from a living organism are myeloid dendritic cells.

The invention also provides CD11b-expressing cells comprising a heterologous antigen or epitope obtainable by the above-defined method.

The invention thus relates to a cell therapy product for immunizing a human or an animal against an antigen, characterized in that it comprises an efficient amount of CD11b expressing cells comprising a heterologous antigen or epitope obtainable by the above-defined method, in combination with a pharmaceutically acceptable vehicle.

The invention further relates to a use of CD11b-expressing cells comprising said antigen or epitope as obtainable by the above-defined method, in the preparation of a cell therapy product for immunizing a human or an animal against an antigen.

More specifically, the invention provides a method for immunizing a patient against an antigen, said method comprising:

a. extracting CD11b expressing cells from said patient,
b. in vitro culturing said CD11b expressing cells with a vector of the invention carrying an antigen or an epitope as a molecule of interest, under conditions appropriate for targeting said vector to said cells,
c. re-administering an efficient amount of said cells comprising said vector to said patient to prime a CD4+ and/or CD8+ response, thereby immunizing said patient to said antigen.

According to a preferred embodiment of the invention, said CD11b-expressing cells are myeloid dendritic cells.

The invention thus also relates to the pharmaceutical composition comprising the vector of the invention carrying an epitope or an antigen as the molecule of interest, in combination with a pharmaceutically acceptable vehicle.

According to one embodiment, said composition is a vaccine suitable for administration in a human or an animal. Preferably, the vaccine is capable of inducing immunity against poliovirus, HIV or a lymphocytic choromeningitidis virus. Of course, the type of immunity induced will depend upon the selected antigen which is carried by the vector. In another embodiment, the vaccine is capable of inducing immunity against whooping cough.

Such vaccines comprise an immunoprotective and non-toxic amount of the vector of the invention. Said composition may further comprise suitable priming adjuvants accordingly.

The invention further relates to a method for immunizing a human or an animal against a pathogen infection, which comprises administering the vaccine comprising an immunoprotective and non toxic amount of the vector of the subject invention to such human or animal.

The invention is also directed to the means for preparing the polypeptides, proteins or the vector of the invention. Especially, those means comprise a nucleic acid encoding one of the following polypeptides:
a. the protein of the invention which is deficient for CD11b/CD18 binding;
b. the polypeptide of the invention which is capable of binding to the CD11b/CD18 integrin; or
c. the vector for targeting a molecule of interest to CD11b expressing cells.

Especially, the nucleic acid of the invention can be derived from the DNA encoding wild-type adenylate cyclase of any *Bordetella* strain using known techniques, e.g., isolating the gene from a gene bank, making complementary or cDNAs from mRNA templates or via the polymerase chain reaction or from isolates of clinical species. Alternatively, the DNA encoding wild-type adenylate cyclase may be synthesized by standard DNA synthesis technique. Various *Bordetella* strains are publicly available from commercial depositories.

Modifications of the wild-type DNA encoding *Bordetella* adenylate cyclase can be obtained by genetic engineering of the wild-type DNA using conventional molecular biology technologies.

Another object of the invention concerns a recombinant nucleic acid constituted by the nucleic acid encoding the polypeptide, the protein or the vector of the invention, cloned into an expression vector appropriate for the expression of the encoded polypeptide or protein in a host cell. Optionally, the recombinant DNA molecule comprise additional coding sequence of a carrier polypeptide which has immunostimulating properties, such as an adjuvant, or which is useful in expressing, purifying and/or formulating the polypeptides of the invention. This coding sequence can be placed in frame with the coding sequence of the polypeptide, protein or vector for targeting molecule of the invention.

The selection of the expression vector will, of course, depend upon the host cell employed.

Preferably, said expression vector is a plasmid, a cosmid, a phagemid or a viral DNA.

The invention is also directed to a method for preparing the protein of the invention deficient for CD11b/CD18 binding; the polypeptide capable of binding CD11b/CD18 as defined above; or the vector for targeting a molecule of interest to CD11b expressing cells, said method comprising the steps of incorporating the recombinant nucleic acid as defined above in an appropriate host cell for the expression of the corresponding polypeptide, protein or vector of interest; culturing the transformed recombinant cells and recovering the synthesized recombinant polypeptide, protein or vector of the invention.

Another aspect of the invention is a host cell transformed with the recombinant nucleic acid of this invention and thus comprising the nucleic acid or the recombinant nucleic acid as defined above. In one embodiment, the recombinant nucleic acid can be integrated into the host cell's genome by conventional techniques, including homologous recombination.

Preferred host cells of the invention include those belonging to the species *E. coli* and the genus *Bordetella*. Other host cells which may be suitable include, but are not limited to, mammalian cells, insect cells, yeast and other bacterial cells.

The invention also encompasses the polyclonal serum obtainable by the immunization of an animal or a human with the polypeptide, the protein, the vector or with the composition of the invention.

In one preferred embodiment, the polyclonal serum is obtainable by the immunization of an animal or a human with the polypeptide consisting of the CD11b/CD18 interaction domain of *Bordetella* adenylate cyclase, preferably the CD11b/CD18 interaction domain of *Bordetella pertussis* adenylate cyclase, extending from amino acid 1166 to amino acid 1281.

The invention also relates to monoclonal antibody directed specifically against the polypeptides of the invention comprising the CD11b/CD18 interaction domain.

In one preferred embodiment, the monoclonal antibody is directed against an epitope located in the CD11b/CD18 interaction domain, preferably against an epitope located in the CD11b/CD18 interaction domain of *Bordetella pertussis* adenylate cyclase, extending from amino acid 1166 to amino acid 1281.

Preferably, said polyclonal serum, or monoclonal antibody is capable of blocking the binding of wild-type adenylate cyclase to CD11b/CD18. The blocking can be assayed by evaluating the capacity of a mixture of said polyclonal serum or monoclonal antibody with a wild-type adenylate cyclase to bind to CD11b/CD18 as compared to the capacity of wild-type adenylate cyclase alone.

In one specific embodiment, said medicament provides passive immunization against *Bordetella* infection.

For use in human organism, the antibodies of the invention can be humanized for instance by the replacement of the hypervariable part of a human immunoglobulin, which has no antibody function, by a hypervariable region of a monoclonal immunoglobulin obtained from the technique described above.

For example, techniques for humanizing antibodies were described by Waldmann T., June 1991, Science, vol. 252, p. 1657-1662; Winter G. et al, 1993, Immunology Today, vol. 14, No. 6, p. 243-246; Carter et al., May 1992, Proc. Natl. Acad. Sci. USA, vol. 89, p. 4285-4289; Singer et al., 1 Apr. 1993, Journal of Immunology, vol. 150, No. 7, p. 2844-2857.

The invention also concerns a pharmaceutical composition, comprising the polyclonal serum or the monoclonal serum, in combination with a pharmaceutically acceptable vehicle.

The invention also relates to the use of a polyclonal serum or a monoclonal to antibody of the invention, in the preparation of a medicament for the treatment, in human or in animal, of disease symptoms associated with whooping cough and/or for protecting a human or an animal against the disease symptoms associated with *Bordetella* infection.

The following experimental part shows the results identifying (i) the role of post-translational acylation in CyaA interaction with CD11b and (ii) the CD11b interaction domain in *Bordetella pertussis* adenylate cyclase.

LEGENDS TO THE FIGURE

FIG. 1. CyaA Binds Specifically to CD11b Cells and Inhibits both CyaA-Biotin and Anti-CD11b Monoclonal Antibody Binding to these Cells (A) CHO cells or CHO-CD11b cells were incubated with the indicated concentrations of CyaA. Surface-bound CyaA was detected by FACS, with anti-CyaA Mab (5G12). Results are expressed as ΔMFI=(MFI value of cells incubated with CyaA)—(MFI value of cells incubated without CyaA) and are representative of at least 2 independent experiments.

(B) CHO-CD11b cells were preincubated with the indicated concentrations of CyaA. Then, CyaA-biotin (30 nM) or anti-CD11b Mab (2 µg/ml) was added separately in the continuous presence of the toxin and their binding was measured by FACS.

(C) After preincubation with the indicated concentrations of CyaA, CHO-CD11b cells or CHO-CD11c cells were incubated with either anti-CD11b or anti-CD11c monoclonal antibody, respectively, in the continuous presence of the toxin. Then, antibody binding was determined by FACS.

For (B) and (C), results are expressed as percentage of binding=(sample binding)/(maximum binding)×100 and are representative of at least 2 independent experiments.

Figure 2:
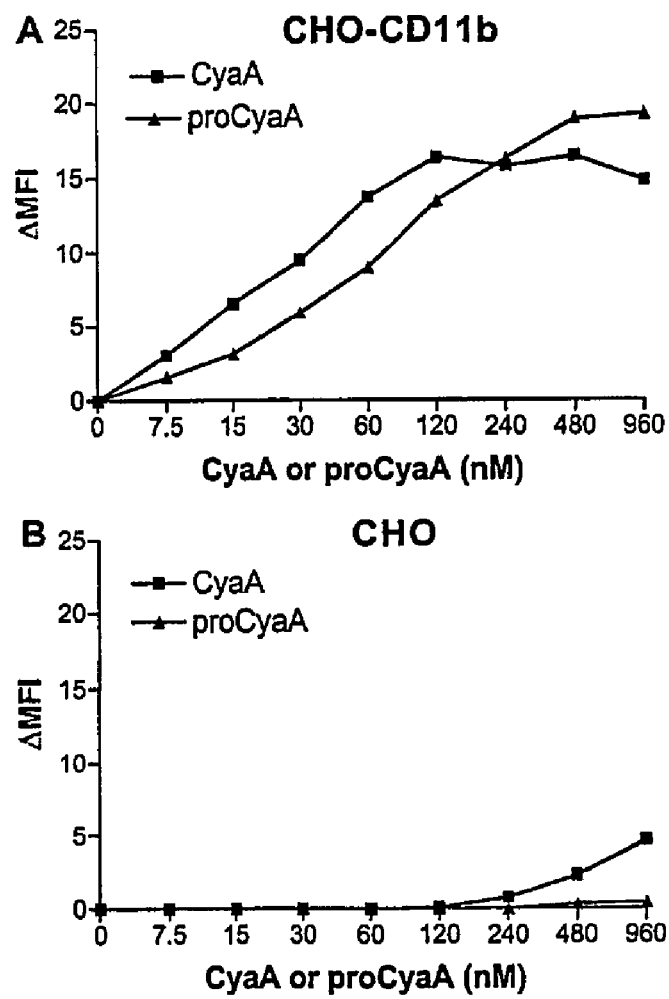

FIG. 2. Direct Binding of CyaA or ProCyaA to CHO Tranfectants.

CHO-CD11b cells (A) or CHO cells (B) were incubated with the indicated concentrations of CyaA or proCyaA. Surface-bound CyaA was detected with anti-CyaA Mab (5G12). Results are expressed as ΔMFI=(MFI value of cells incubated with CyaA)—(MFI value of cells incubated without CyaA) and are representative of 2 independent experiments.

Figure 3:
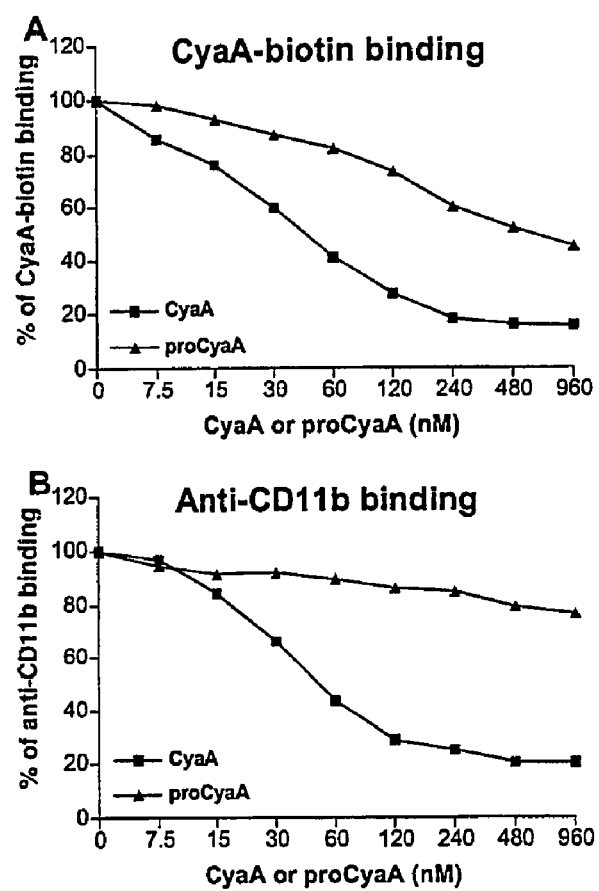

FIG. 3. CyaA Acylation is Required for Stable Association with CHO-CD11b Cells

CHO-CD11b cells were preincubated with the indicated concentrations of CyaA or proCyaA. CyaA-biotin (A) or anti-CD11b Mab (B) was then added, in the continuous presence of CyaA or proCyaA. Surface bound CyaA-biotin or anti-CD11b Mab was measured by FACS. Results are expressed as percentage of binding=(sample binding)/(maximum binding)×100 and are representative of at least 2 independent experiments.

Figure 4:
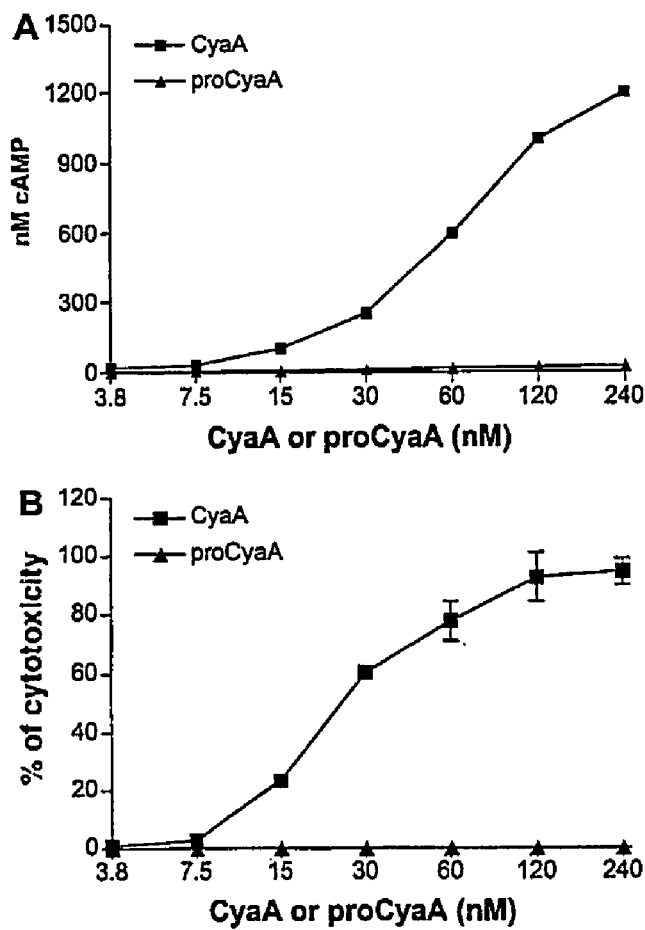

FIG. 4. CyaA Acylation is Required for CyaA Induced-cAMP Accumulation and Cytotoxicity CHO-CD11b cells were incubated with either CyaA or proCyaA at the indicated concentrations for 20 min at 37° C. Then, cells were lysed and cAMP was measured (A). In parallel, toxicity was determined by measuring the amount of lactate dehydrogenase released in the medium after incubation of CHO-CD11b cells for 4 hours at 37° C. in the presence of the indicated concentrations of either CyaA or proCyaA (B). Results are representative of at least 2 independent experiments.

Figure 5:
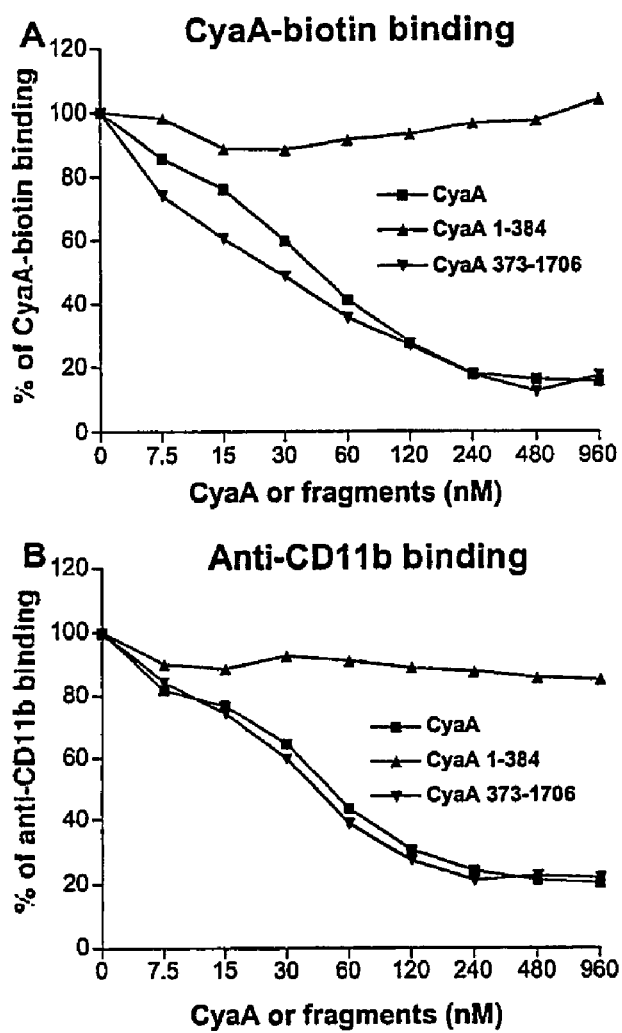

FIG. 5. The Catalytic Domain is not Required for CyaA Interaction with CD11b Cells CHO-CD11b cells were preincubated with the indicated concentrations of CyaA, CyaA 1-384 or CyaA 373-1706. Cells were then incubated with either CyaA-biotin (A) or anti-CD11b Mab (B). Binding of CyaA-biotin and anti-CD11b Mab was measured by FACS. Results are expressed as percentage of binding=(sample binding)/(maximum binding)×100 and are representative of at least 2 independent experiments.

Figure 6:
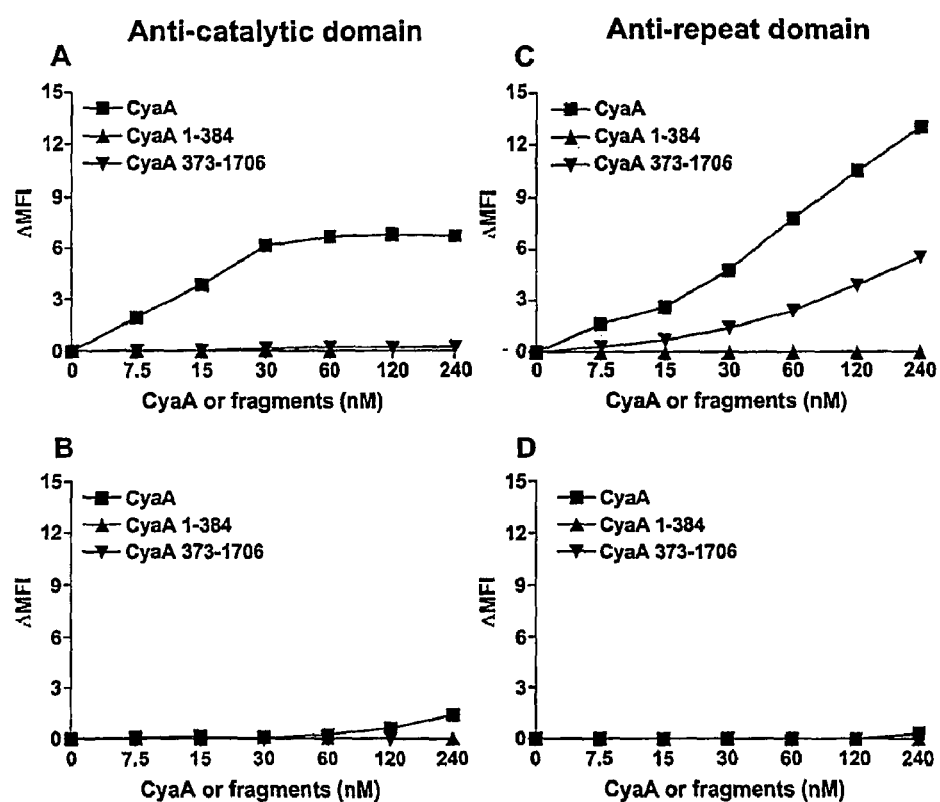

FIG. 6. Direct Binding of CyaA Fragments to CD11b Cells

CHO-CD11b cells (A, C) or CHO cells (B, D) were incubated with the indicated concentrations of CyaA, CyaA 1-384 and CyaA 373-1706. Then, surface—bound CyaA was detected with anti-CyaA 5G12 Mab that recognizes the catalytic domain (A, B) or with anti-CyaA 6D7 Mab that recognizes the repeat domain (C, D). Results are expressed as ΔMFI=(MFI value of cells incubated with CyaA or CyaA fragments)−(MFI value of cells incubated without CyaA or CyaA fragments) and are representative of at least 2 independent experiments.

Figure 7:
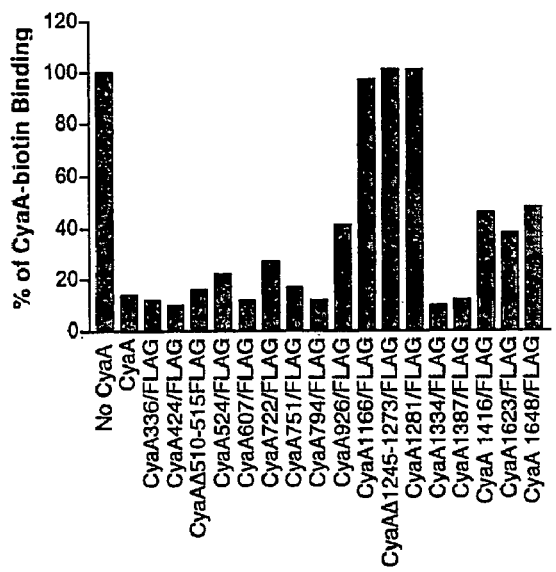

FIG. 7. CyaA-Biotin Binding to CHO-CD11b Cells in the Presence of CyaA-FLAG Mutants CHO-CD11b cells were preincubated with CyaA or CyaA FLAG mutants (30 nM). Then, CyaA-biotin was added, in the continuous presence of CyaA or CyaA-FLAG molecules. Surface bound CyaA-biotin was detected by FACS with streptavidin-PE. Results are expressed as percentage of binding=(sample binding)/(maximum binding)×100 and are representative of at least 2 independent experiments.

Figure 8:
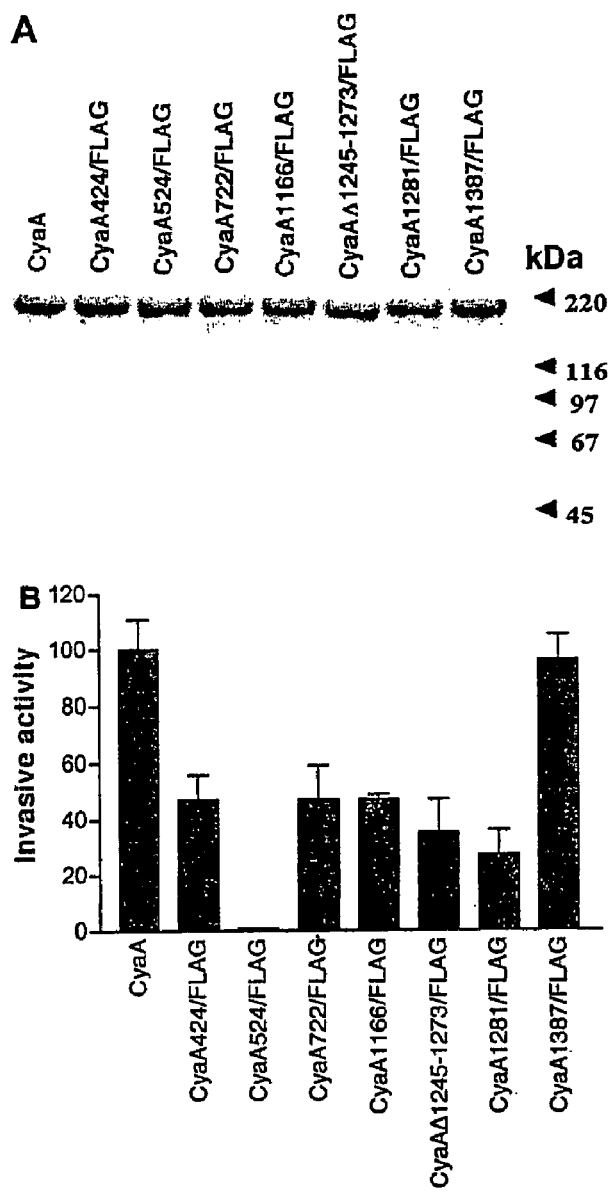

FIG. 8. SDS-Page Analysis of the Purified CyaA Preparations and Their Invasive Activity on Erythrocytes (A) CyaA/FLAG molecules together with the wild type CyaA were purified from urea extracts by DEAE- and Phenyl sepharose chromatographies as previously described (Karimova et al., 1998). About 3 μg of each protein was analyzed on a 7.5% acrylamide gel stained with Coomassie blue. (B) Invasive activity of CyaA/FLAG molecules on sheep erythrocytes. Two micrograms of various CyaA proteins were incubated with $5\times10^8$ washed sheep erythrocytes for 30 minutes and the amount of AC activity translocated into the cells was determined as previously described (Osicka et al., 2000). The values represent the average from three experiments performed in duplicates (n=6).

Figure 9:
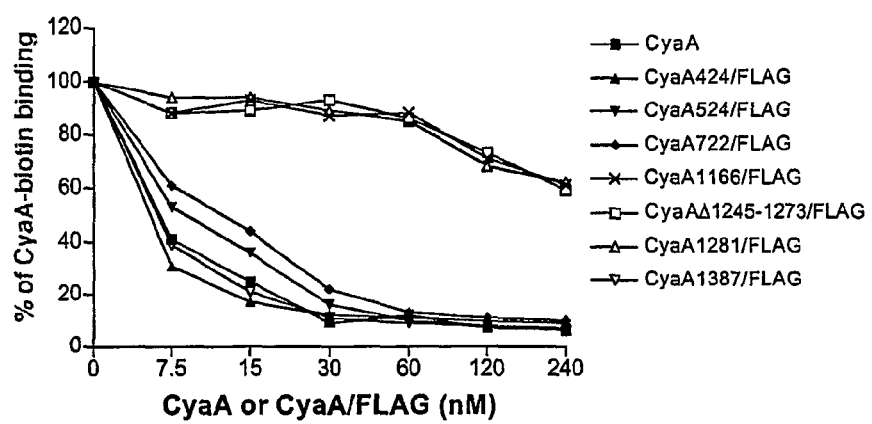

FIG. 9. CyaA Binding to CHO-CD11b Cells in the Presence of Selected CyaA-FLAG Mutants CHO-CD11b cells were preincubated with CyaA or CyaA FLAG mutants at various concentrations ranging from 7.5 nM to 240 nM. CyaA-biotin was added, in the continuous presence of CyaA molecules and surface bound CyaA-biotin was revealed. Results are expressed as percentage of binding=(sample binding)/(maximum binding)×100 and are representative of at least 2 independent experiments.

EXPERIMENTAL PART

A. Material and Methods

A.1 Production, Purification and Modification of the CyaA-Derived Proteins

DNA manipulations were performed according to standard protocols (Sambrook et al., 1989) in the *Escherichia coli* strain XL1-Blue (Stratagene, Amsterdam, Netherlands) as host cells. The plasmids coding for a non-acylated wild type proCyaA (pACT7), acylated wild type CyaA (pT7CACT1) and a recombinant detoxified CyaA-E5-CysOVA harbouring a unique cysteine residue and the OVA epitope in its catalytic domain (pCACT-E5-CysOva) were already described (Gmira et al., 2001; Guermonprez et al., 2001; Osicka et al., 2000; Sebo et al., 1991). The plasmid encoding CyaA 373-1706 (pTRCyaAΔ1-373) is a derivative of pTRCAG (Gmira et al., 2001) in which the DNA sequence coding for the catalytic domain of the toxin (comprised between the NdeI and BstBI sites) was deleted and replaced by an appropriate synthetic double stranded oligonucleotide encoding the amino acid sequence: Met-Gly-Cys-Gly-Asn.

Protocol for CyaA production has already been described elsewhere (Karimova et al., 1998). All proteins were expressed in *E. coli* BLR strain (Novagen, Merck KG, Darmstadt, Germany), and were purified to more than 95% homogeneity (as judged by SDS-gel analysis) from inclusion bodies by a two-step procedure including DEAE-Sepharose and Phenyl-sepharose chromatographies as described in Guermonprez et al., 2000. Purified CyaA-E5-CysOVA protein was labeled on its unique cysteine residue with the sulfhydryl reagent N-(6-(Biotinamido)hexyl)-3'-(2'-pyridyldithio) propiamide (Biotin-HPDP) (Pierce, Bezons, France) according to the manufacturer's instructions. The biotinylated-CyaA was re-purified on DEAE-Sepharose in order to remove the unreacted Biotin-HPDP reagent. CyaA-1-384 was expressed and purified as described in Ladant et al., 1992.

Toxin concentrations were determined spectrophotometrically from the adsorption at 278 nm using a molecular extinction coefficient of 141 $mM^{-1}$ $cm^{-1}$ for the full length CyaA toxins, 113 $mM^1$ $cm^{-1}$ for the CyaA 373-1706 and 28 $mM^{-1}$ $cm^{-1}$ for CyaA 1-384.

The CyaA-FLAG molecules were constructed using the previously defined permissive insertion sites along the CyaA molecule (Osicka et al., 2000). We generated a set of 17 CyaA constructs, which carried at the individual permissive positions a synthetic octapeptide insert Asp-Tyr-Lys-Asp-Asp-Asp-Asp-Lys for the FLAG epitope (Sigma, Saint Quentin Fallavier, France). To achieve this, three double stranded synthetic oligonucleotide pairs (5'-GTACTGATTATAAA-GATGACGATGACAAATCAC+5'-GTACGTGATTTGT-CAT CGTCATCTTTATAATCA, 5'-GTACTTATCGAT-TATAAAGATGACGATGACAAA 5'-GTACTTTGTCATCGTCATCTTTATAATCGATAA and 5'-GTACGTGGATTATAAA GATGACGATGACAAAGC 5'-GTACGCTTTGTCATCGTCATCTTTATAATCCAC, respectively) (SEQ ID NOs: 5 to 10), encoding the FLAG epitope in the required reading frames, were inserted into the unique BsrG I sites previously introduced within the cyaA (Osicka et al., 2000). Correct insertions were checked by DNA sequencing, the recombinant CyaA molecules were expressed in $E.\ coli$ and purified. The invasive capacity of selected CyaA/FLAG molecules were characterized, using sheep erythrocytes as target cells as previously described (Osicka et al., 2000).

A.2 Production of Anti-CyaA Monoclonal Antibodies

BALB/c mice were initially immunized intraperitoneally with CyaA toxin (20 µg in alum). At approximately two weeks interval, mice were boosted with 10 µg CyaA in alum for 3 times. Throughout the immunization protocol, mice were bled and their sera tested for the presence of anti-CyaA antibodies by ELISA. When significant sera titers were detected, a last boost was given to these mice and their splenocytes were fused with P3X63 myeloma cells (ATCC, Manassas, USA) 3 days later. The generated hybridomas were screened for the production of CyaA specific monoclonal antibodies by ELISA. Highly productive hybridomas were then selected and cloned by single-cell limiting dilutions and subsequently used to make ascites in BALB/c nude mice to generate large amounts of anti-CyaA monoclonal antibodies. The monoclonal antibodies were purified from ascites using T-GelTM purification kit (Pierce, Bezons, France) according to manufacturer instructions. The antibody concentration was measured with Bio-Rad protein assay (Bio-Rad, Marnes la Coquette, France). Two of these monoclonal antibodies were used in this study: antibody 5G12 that reacts with an epitope localized within amino acid 1 to 190, and antibody 6D7 that reacts with an epitope localized within amino acids 1006 to 1706.

A.3 Cells and Culture

Chinese Hamster Ovary cells transfected with human CD11b/CD18 (CHO-CD11b cells), human CD11c/CD18 (CHO-CD11c cells) or transfected with the vector alone (CHO cells) were a kind gift of D. Golenbock (Boston University School of Medicine, Boston, Mass.) and were cultured in the presence of neomycin as described previously (Ingalls et al., 1998).

A.4 Antibodies

Monoclonal antibodies specific for human CD11b (ICRF44, mouse IgG1, κ) and human CD11c (B-Ly6, mouse IgG1, κ) were purchased from BD Pharmingen (Le Pont de Claix, France).

A.5 Binding Assays

The assays were performed as described in Guermonprez et al., 2001. Briefly, $2 \times 10^5$ cells were incubated with the indicated concentrations of CyaA molecules in DMEM medium containing 4.5 mg/ml glucose (Life Technologies, Cergy Pontoise, France), without serum, in 96-well culture plates for 30 min on ice. After washing, anti-CyaA catalytic domain Mab (5G12) or anti-CyaA repeat domain Mab (6D7) was added at 25 µg/ml. In some experiments, cells were preincubated with the indicated concentrations of CyaA molecules for 30 min on ice. Then, CyaA-biotin (30 nM), anti-CD11b Mab (2 µg/ml) or anti-CD11c Mab (2 µg/ml) (BD Pharmingen) were added separately in the continuous presence of the toxins.

After washing and removing supernatant, cells were stained with goat anti-mouse IgG-PE (Caltag, Le Perray en Yvelines, France) or with streptavidin-PE (BD Pharmingen) at 1:300 dilution. After the last wash, cells were analyzed by flow cytometry on a FACStar™ (Becton Dickinson, Le Pont de Claix, France) in the presence of 5 µg/ml propidium iodide. Aggregated and dead cells were substracted by gatings based on propidium idiode exclusion. The binding data were deduced from the mean fluorescence intensity (MFI) and expressed as ΔMFI=(MFI value of cells incubated with CyaA)–(MFI value of cells incubated without CyaA) or as percentage of binding=(sample binding)/(maximum binding)×100. The maximum binding corresponds to (MFI value of cells incubated with CyaA or anti-CD11b in the absence of competitor)–(MFI value of cells incubated with medium alone). The sample binding corresponds to (MFI value of cells incubated with CyaA or anti-CD11b in the presence of competitor)–(MFI value of cells incubated with medium alone).

A.6 cAMP Assay

Cyclic AMP accumulated in cells exposed to the CyaA toxin was performed essentially as described in Guermonprez et al., 2001. Briefly, $5 \times 10^5$ cells were incubated with the indicated concentrations of CyaA in DMEM+glucose for 20 min at 37° C. After washing, cAMP accumulated in cell cytosol was released by lysis with 0.1 N HCl and boiling for 5 min at 120° C. After neutralization with 0.1 N NaOH, the samples were then added to microtiter plates previously coated with a cAMP-BSA conjugate and, then incubated with an appropriate dilution of anti-cAMP rabbit antiserum. After washing, anti-cAMP antibodies were revealed with anti-rabbit antibodies coupled to alkaline phosphatase. The cAMP content of each sample was determined from comparison with a standard curve obtained by adding known cAMP concentration.

A.7 CyaA Invasive Activity

Invasive activity of CyaA molecules was determined as described previously in Osicka et al., 2000. Briefly, sheep erythrocytes were incubated with toxin for 30 min and the invasive activity was measured as the AC activity translocated into erythrocytes and protected against digestion by extracellularly added trypsin.

B. Results

B.1 CyaA Specifically Binds to CD11b⁺ Cells and Inhibits CyaA-biotin and Anti-CD11b Binding to CD11b⁺ Cells In order to investigate the role of biological and structural properties of CyaA in its interaction with CD11b, two complementary assays were developed; a binding assay and a competition assay. The binding assay consisted in incubation of CyaA molecules with transfected CHO cells expressing human CD11b/CD18 (CHO-CD11b cells), or with mock transfected CHO cells and subsequent detection of the cell-associated toxin with an anti-CyaA monoclonal antibody (5G12) specific for the catalytic domain. As shown in FIG. 1A, using this assay, CyaA binding was specifically detected on CD11b⁺ cells. In the competition assay, different CyaA molecules (mutants or fragments) can be tested for their ability to compete with CyaA-biotin, or anti-CD11b monoclonal antibody (Mab) binding to CD11b+ cells. Here, the CHO-CD11b cells were incubated with CyaA at different concentrations for 30 minutes on ice. Then, in the continuous presence of CyaA, CyaA-biotin (30 nM) or anti-CD11b Mab (2 μg/ml) were added and their binding to the cells was evaluated by FACS. As shown in FIG. 1B, CyaA efficiently inhibited both CyaA-biotin and anti-CD11b binding to CHO-CD11b cells in a dose dependent manner. This inhibitory effect was specific for CD11b since CyaA was completely unable to compete with another ligand (anti-CD11c Mab) for its specific receptor (CD11c) expressed by CHO cells (FIG. 1C).

B.2 Lack of CyaA Acylation Affects its Binding to CD11b+ Cells

Since it is well established that CyaA needs a posttranslational palmitoylation to perform its invasive activity and to form hemolytic membrane channels, we tested whether the lack of acylation affects CyaA interaction with CD11b+ cells. In a binding assay, CHO cells or CHO-CD11b cells were incubated with either CyaA or non acylated proCyaA. The binding was evaluated using anti-CyaA catalytic domain Mab (5G12). As shown in FIG. 2A, at low concentrations, binding of both CyaA and proCyaA molecules to CD11b+ cells was rather comparable, with a slightly more efficient binding of the acylated CyaA. This could be due to its enhanced interaction with cell membrane, a better adapted conformation of CyaA for binding and/or higher affinity of CyaA for the CD11b receptor. Indeed, the proCyaA binding reached saturation at substantially higher protoxin concentrations, as compared to CyaA binding. The simplest explanation of this observation could be that proCyaA binds CD11b+ cells with lower affinity than CyaA. At high protoxin concentration, aggregates and/or oligomers of proCyaA would bind to the cells and, consequently, higher amounts of proCyaA are found to be bound by the antibody detection system. In contrast, very low binding of CyaA or proCyaA to control CHO cells was detected (FIG. 2B).

B.3 Acylation Stabilizes Interaction of CyaA with CD11b+ Cells

To further analyze the role of CyaA acylation in interaction of the toxin with CD11b+ cells, we tested the ability of non-acylated proCyaA to compete with CyaA for binding to CHO-CD11b cells. As shown in FIG. 3A, when compared to the acylated CyaA, the non-acylated proCyaA exhibited a significantly reduced capacity to compete with biotinylated CyaA for binding to CD11b+ cells. To determine if the lack of inhibition was due to an inefficient interaction with CD11b, we evaluated the capacity of proCyaA to block anti-CD11b binding to CHO-CD11b cells. Indeed, compared to CyaA, proCyaA was unable to inhibit anti-CD11b binding to CHO-CD11b cells (FIG. 3B).

Since supraphysiological production of cAMP and cell intoxication are the consequences of CyaA interaction with CD11b+ cells, we then analyzed, using CHO-CD11b cells, if these toxin functions are dependent on CyaA acylation. As expected, in contrast to the acylated toxin, proCyaA did not induce any cAMP increase in CHO-CD11b cells (FIG. 4A) and had no significant cytotoxic effect on these cells (FIG. 4B). Taken together, these results clearly demonstrate that acylation of CyaA is necessary for a functional interaction of the toxin with CD11b+ cells and that the binding of proCyaA to CD11b is insufficient to trigger cytotoxic effects on CD11b-expressing cells.

B.4 The Catalytic Domain is not Required for cyaA Interaction with CD11b

Functionally, CyaA is composed of two main domains harboring independent activities. The N-terminal domain harbors the adenylate cyclase activity (aminoacids 1-400), whereas the carboxy-terminal hemolysin moiety (aminoacids 400-1706) is responsible for the delivery of the AC domain into target cells and the hemolytic activity of B. pertussis. To examine the role of these two functional domains of CyaA in binding to CD11b+ cells, we tested the ability of the catalytic domain encoded by residues 1 to 384, CyaA 1-384, and of the hemolytic moiety, encoded by residues 373-1706, CyaA 373-1706, to compete for binding to CHO-CD11b cells with CyaA-biotin. As shown in FIG. 5A, the catalytic domain was unable to inhibit CyaA-biotin binding to CHO-CD11b cells whereas CyaA 373-1706 exhibited the same binding inhibition as the full-length CyaA. Similarly, the catalytic domain was also unable to inhibit binding of the anti-CD11b Mab to CHO-CD11b cells (FIG. 5B). Moreover, direct binding assays with an anti-CyaA Mab (5G12) specific for the catalytic domain, could not reveal any significant association of CyaA 1-384 to the surface of CHO-CD11b cells, while binding of CyaA was readily detected (FIG. 6A). Direct binding of CyaA 373-1706 to CHO-CD11b cells could not be detected with the 5G12 Mab which recognizes an epitope located within the first 200 amino acids of CyaA, but was clearly demonstrated by using another anti-CyaA Mab (6D7), specific for the repeat domain (FIG. 6C). Again, only very weak binding of CyaA or CyaA 373-1706 was detected with the 6D7 Mab on CHO cells lacking CD11b (FIGS. 6B and D). Altogether, these results clearly demonstrate that catalytic domain is not necessary for CyaA interaction with CD11b and that the CyaA/CD11b interaction domain is located in the CyaA 373-1706 fragment.

B.5 CyaA Domain Interacting with CD11b is Located within the CyaA Repeat Region

To identify the region of CyaA that interacts with CD11b, we expressed and purified different sub-fragments of the C-terminal region CyaA 373-1706 (encompassing residues 373-1490, or 700-1706, or 700-1490, or 1006-1706) that were tested in the competition assay. However, none of these polypeptides were able to compete in a significant manner with the binding of CyaA-biotin to CHO-CD11b cells. This might be due to the fact that these isolated fragments adopt an altered conformation. Therefore, we used a mutational approach to locate the CD11b binding domain of CyaA. Seventeen different modified CyaA molecules were constructed by insertion of the FLAG epitope (of amino acid sequence: DYKDDDDK) at various defined positions throughout the toxin polypeptide as detailed in Material and Methods. We hypothesized that insertion of a heterologous and highly charged peptide at certain positions of the CD11b-binding domain might disrupt its capacity to interact with CD11b. The 17 FLAG-tagged CyaA molecules were expressed and purified to homogeneity and tested for the capacity to inhibit binding of CyaA-biotin to CHO-CD11b cells (note that in two cases, CyaAΔ510-515/FLAG and CyaAΔ1245-1273/FLAG, the amino acids 510 to 515 or 1245 to 1273 of CyaA, respectively were deleted and replaced by the inserted FLAG epitope). As shown in FIG. 7, insertion of the FLAG epitope at 3 different sites located between residues 1166-1281 totally abrogated the interaction with CD11b. The corresponding modified CyaA were essentially unable to compete with CyaA-biotin for CD11b binding, when tested at 30 nM concentrations. In contrast, all other FLAG-tagged recombinant CyaAs were able to compete with CyaA-biotin for binding to CD11b+ cells, although with variable efficiency. Noticeably, the three recombinant CyaA constructs with the FLAG epitope inserted close to the carboxy-terminal end of the protein (i.e. at position, 1416, 1623 and 1648) were also partially impaired in their capacity to compete for CD11b binding with CyaA-biotin.

To further characterize the CyaA domain that interacts with CD11b, we focused on the three CyaA/FLAG molecules that failed to inhibit CyaA-biotin binding to CD11b$^+$ cells, in addition to four other CyaA/FLAG molecules shown to bind CD11b$^+$ cells as efficiently as intact CyaA. These CyaA molecules were again expressed and purified close to homogeneity (FIG. 8A) and their cell-invasive activity was examined by analyzing their capacity to penetrate sheep erythrocyte membranes (RBC) and to deliver the catalytic domain into a compartment inaccessible to externally added trypsin. As shown in FIG. 8B, except for CyaA1387/FLAG, the invasive activity of all other tested CyaA/FLAG molecules was affected to some extent by insertion of the FLAG peptide. The invasive activity of CyaA524/FLAG, which reflects the capacity of CyaA to translocate the catalytic domain into erythrocytes, was completely ablated by the insertion of the FLAG peptide at residue 524. The capacities of the other proteins, CyaA424/FLAG, CyaA722/FLAG and CyaA1166/FLAG and, to a lesser extent, of CyaAΔ1245-1273/FLAG and CyaAΔ1281/FLAG proteins to penetrate into RBC were, however, comparable.

The ability of these molecules to compete with CyaA-biotin for binding to CHO-CD11b cells was tested in a dose dependent manner, as shown in FIG. 9. As expected, the CyaA1166/FLAG, CyaAΔ1245-1273/FLAG, and CyaAΔ1281/FLAG proteins were unable to inhibit CyaA-biotin binding to CD11b$^+$ cells, even at concentrations as high as 240 nM. In contrast, all other CyaA/FLAG constructs inhibited the CyaA-biotin binding in a dose dependent manner, similarly to intact CyaA. The lack of inhibition of binding by CyaA1166/FLAG, CyaAΔ1245-1273/FLAG and CyaA1281/FLAG could, hence, not be attributed to a generalized conformational disruption of the toxin caused by FLAG insertion, because the invasive activity of these constructs on RBC was comparable to the activity of CyaA424/FLAG protein, which interacted very efficiently with CD11b$^+$ cells.

In conclusion, these results provide a compelling evidence that the portion of the CyaA RTX repeat domain delimited by residues 1166 and 1281 and comprising a predicted loop (residues 1208-1243) located between two conserved RTX repeat blocks (Osicka et al., 2000), is crucial for interaction of CyaA with CD11b$^+$ cells and it most likely represents the main integrin-binding domain of CyaA.

C. Discussion

The biological activity of the adenylate cyclase toxin (ACT or CyaA) is entirely dependent on a covalent post-translational fatty-acylation. In the absence of acylation of the conserved Lys-983 residue, CyaA cannot deliver its catalytic domain into erythrocyte cytosol and is unable to form hemolytic channels (Barry et al., 1991; Basar at al., 2001; Hackett et al., 1994). CyaA was shown to penetrate with detectable efficiency a large variety of eukaryotic cells. It was, however, demonstrated that its primary target cells are myeloid cells such as neutrophils and lung macrophages that are particularly sensitive to CyaA and are paralyzed and committed to apoptosis upon exposure to CyaA (Confer and Eaton, 1982; Khelef and Guiso, 1995; Khelef et al., 1993). We have, indeed, recently shown that the toxin has a specific cellular receptor, an $\alpha_M\beta_2$ integrin (CD11b/CD18), which is exclusively expressed on immune cells such as neutrophiles, macrophages or dendritic cells and that expression of CD11b most likely accounts for the high sensitivity of these cells to CyaA (Guermonprez at al., 2001). In the present study, the inventors showed that CyaA acylation plays a major role in its interaction with CD11b$^+$ cells. Indeed, albeit non-acylated proCyaA was able to bind CD11b$^+$ cells as efficiently as CyaA, it was inefficient in competing with acylated CyaA for binding to CHO-CD11b$^+$ cells and was completely unable to block anti-CD11b Mab binding to these cells. This suggests that while still interacting with CD11b, the nature of interaction and in particular the affinity and/or stability of the proCyaA-CD11b complex differs significantly from that involved in CD11b interaction of the mature CyaA. Moreover, although proCyaA is still able to bind the CD11b receptor, this interaction does not allow membrane penetration of the protoxin. Hence, the acylation may be needed to confer a translocation-competent conformation of CyaA that is required for the delivery of the catalytic domain to the cell cytosol where it can catalyze the conversion of ATP to cAMP.

Functionally, CyaA can be divided in two main domains; one endowed with adenylate cyclase activity domain located between residues 1 to 400, and one responsible for hemolytic activity located within residues 400 to 1706 (Ladant and Ullmann, 1999). After toxin interaction with target cells, the catalytic domain can be directly translocated across the plasma membrane of erythrocytes. The present data show that albeit the catalytic domain plays a key role in the cytotoxic activity of CyaA by catalyzing conversion of ATP to cAMP, this domain is not required for binding of CyaA to its receptor. These results further show that the CyaA/CD11b interaction domain is located in the hemolysin moiety and more precisely in a portion of the glycine- and aspartate-rich RTX repeat region comprising residues 1166 to 1281, as delineated by the insertion sites of the FLAG epitope in constructs with strongly affected binding to CD11b$^+$ cells. In particular, a predicted loop structure interposed between two RTX repeat blocks and comprising the residues 1208 to 1243 (Osicka et al., 2000), could play a crucial role in interaction of CyaA with CD11b$^+$ cells. The loss of interaction with CD11b of the CyaA1166/FLAG, CyaAΔ1245-1273 and CyaA1281/FLAG constructs, respectively, could be due to structural alterations selectively affecting a functionally essential segment involved specifically in the interaction of the CyaA protein with CD11b. This appears much plausible, since all three constructs that failed to bind CD11b still exhibited a substantial cell-invasive activity (20% to 50% of that of intact CyaA) in the surrogate assay system on erythrocytes, where toxin activity does not depend on interaction with CD11b. This indicates that FLAG insertions at positions 1166, 1245 and 1281, did not impair the overall structure of CyaA but rather selectively ablated the capacity of those constructs to interact with the CD11b$^+$ cells. Altogether these results suggest that residues 1166 to 1281 of CyaA delineate an essential portion of the integrin binding domain involved in toxin interaction with the $\alpha_M\beta_2$ integrin (CD11b/CD18).

This conclusion is supported by results showing that all CyaA variants with FLAG peptide inserted within the first 800 residues of CyaA fully competed for binding to CD11b with biotinylated intact CyaA. In contrast, the CD11b-binding capacity was somewhat reduced also for proteins CyaA1416/FLAG, CyaA/FLAG1623 and CyaA/FLAG1648, suggesting that an accessory CD11b-interacting domain of CyaA might be located towards the carboxy-terminal end of the RTX repeat portion of the toxin.

The present results that identify the region 1166-1287 as a major CD11b binding motif of CyaA offer an attractive explanation for the previous observation that binding of CyaA to CD11b was strictly calcium-dependent (Guermonprez et al., 2001). As the RTX domain is involved in calcium-binding and undergoes major structural rearrangement upon calcium binding (Rose et al., 1995), one can speculate that the CD11b binding motif located in the region 1166-1287 might be exposed only in the calcium-bound conformation of RTX domain. The CD11b binding motif identified here within the amino-acid region 1166-1287 of CyaA, is precisely localized between the second and $3^{rd}$ block of RTX repeats. One can hypothesize that the α-helical structuration of this segment is involved in the formation of a docking site for CD11b.

CyaA has been used in several passive and active protection protocols in mouse models of pertussis. Immunization with anti-CyaA specific antibodies or with purified CyaA reduced the time course of the respiratory tract colonization by B. pertussis and protected the mice against a lethal intranasal infection (Guiso et al., 1989; Guiso et al., 1991). Moreover, antibodies specific for CyaA were detected in the sera of human infants infected with B. pertussis (Arciniega et al., 1991; Guiso et al., 1993). The present results suggest that a CyaA molecule lacking CyaA/CD11b interaction domain can be designed for the production as a safe acellular vaccine for protection against B. pertussis infection. The catalytic activity of such a molecule can be easily inactivated by dipeptide insertions within the ATP-binding site, located between residues 188 and 189 of CyaA (Fayolle et al., 1996), while the deletion within the CD11b interaction domain could preserve immune cells from potentially negative effects, such as signaling upon the integrin engagement by the toxoid and/or some functional interference due to competition for binding to CD11b with the CyaA toxoid, which also serves as the complement receptor CR3.

In conclusion, the present data provide important new insights into the role of acylation and of different domains of the adenylate cyclase of B. pertussis in its interaction with CD11b$^+$ cells as well as in the subsequent biological activities triggered by this interaction.

BIBLIOGRAPHY

Altieri, D. C. and Edgington, T. S. (1988) The saturable high affinity association of factor X to ADP-stimulated monocytes defines a novel function of the Mac-1 receptor. *J Biol Chem*, 263, 7007-7015.

Arciniega, J. L., Hewlett, E. L., Johnson, F. D., Deforest, A., Wassilak, S. G., Onorato, I. M., Manclark, C. R. and Burns, D. L. (1991) Human serologic response to envelope-associated proteins and adenylate cyclase toxin of Bordetella pertussis. *J Infect Dis*, 163, 135-142.

Arnaout, M. A. (1990) Structure and function of the leukocyte adhesion molecules CD11/CD18. *Blood*, 75, 1037-1050.

Barry, E. M., Weiss, A. A., Ehrmann, I. E., Gray, M. C., Hewlett, E. L. and Goodwin, M. S. (1991) Bordetella pertussis adenylate cyclase toxin and hemolytic activities require a second gene, cyaC, for activation. *J Bacteriol*, 173, 720-726.

Basar, T., Havlicek, V., Bezouskova, S., Hackett, M. and Sebo, P. (2001) Acylation of lysine 983 is sufficient for toxin activity of Bordetella pertussis adenylate cyclase. Substitutions of alanine 140 modulate acylation site selectivity of the toxin acyltransferase CyaC. *J Biol Chem*, 276, 348-354.

Bell, D., Young, J. W. and Banchereau, J. (1999) Dendritic cells. *Adv Immunol*, 72, 255-324.

Bellalou, J., Sakamoto, H., Ladant, D., Geoffroy, C. and Ullmann, A. (1990) Deletions affecting hemolytic and toxin activities of Bordetella pertussis adenylate cyclase. *Infect Immun*, 58, 3242-3247.

Beller, D. I., Springer, T. A. and Schreiber, R. D. (1982) Anti-Mac-1 selectively inhibits the mouse and human type three complement receptor. *J Exp Med*, 156, 1000-1009.

Confer, D. L. and Eaton, J. W. (1982) Phagocyte impotence caused by an invasive bacterial adenylate cyclase. *Science*, 217, 948-950.

Diamond, M. S. and Springer, T. A. (1993) A subpopulation of Mac-1 (CD11b/CD18) molecules mediates neutrophil adhesion to ICAM-1 and fibrinogen. *J Cell Biol*, 120, 545-556.

Diamond, M. S., Staunton, D. E., de Fougerolles, A. R., Stacker, S. A., Garcia-Aguilar, J., Hibbs, M. L. and Springer, T. A. (1990) ICAM-1 (CD54): a counter-receptor for Mac-1 (CD11b/CD18). *J Cell Biol*, 111, 3129-3139.

Fayolle, C., Sebo, P., Ladant, D., Ullmann, A. and Leclerc, C. (1996) In vivo induction of CTL responses by recombinant adenylate cyclase of Bordetella pertussis carrying viral CD8+ T cell epitopes. *Journal of Immunology*, 156, 4697-4706.

Friedman, R. L., Fiederlein, R. L., Glasser, L. and Galgiani, J. N. (1987) Bordetella pertussis adenylate cyclase: effects of affinity-purified adenylate cyclase on human polymorphonuclear leukocyte functions. *Infect Immun*, 55, 135-140.

Gmira, S., Karimova, G. and Ladant, D. (2001) Characterization of recombinant Bordetella pertussis adenylate cyclase toxins carrying passenger proteins. *Res Microbiol*, 152, 889-900.

Goodwin, M. S. and Weiss, A. A. (1990) Adenylate cyclase toxin is critical for colonization and pertussis toxin is critical for lethal infection by Bordetella pertussis in infant mice. *Infect Immun*, 58, 3445-3447.

Gray, M. C., Ross, W., Kim, K. and Hewlett, E. L. (1999) Characterization of binding of adenylate cyclase toxin to target cells by flow cytometry. *Infect Immun*, 67, 4393-4399.

Gueirard, P., Druilhe, A., Pretolani, M. and Guiso, N. (1998) Role of adenylate cyclase-hemolysin in alveolar macrophage apoptosis during Bordetella pertussis infection in vivo. *Infect Immun*, 66, 1718-1725.

Guermonprez, P., Fayolle, C., Karimova, G., Ullmann, A., Leclerc, C. and Ladant, D. (2000) Bordetella pertussis adenylate cyclase toxin: a vehicle to deliver CD8-positive T-cell epitopes into antigen-presenting cells. *Methods Enzymol*, 326, 527-542.

Guermonprez, P., Fayolle, C., Rojas, M. J., Rescigno, M., Ladant, D. and Leclerc, C. (2002) In vivo receptor-mediated delivery of a recombinant invasive bacterial toxoid to CD11c+CD8alpha-CD11b$^{high}$ dendritic cells. *Eur J Immunol*, 32, 3071-3081.

Guermonprez, P., Khelef, N., Blouin, E., Rieu, P., Ricciardi-Castagnoli, P., Guiso, N., Ladant, D. and Leclerc, C. (2001) The adenylate cyclase toxin of Bordetella pertussis binds to target cells via the alpha(M)beta(2) integrin (CD11b/CD18). *J Exp Med*, 193, 1035-1044.

Guiso, N., Grimprel, E., Anjak, I. and Begue, P. (1993) Western blot analysis of antibody responses of young infants to pertussis infection. *Eur J Clin Microbiol Infect Dis*, 12, 596-600.

Guiso, N., Rocancourt, M., Szatanik, M. and Alonso, J. M. (1989) Bordetella adenylate cyclase is a virulence associated factor and an immunoprotective antigen. *Microb Pathog*, 7, 373-380.

Guiso, N., Szatanik, M. and Rocancourt, M. (1991) Protective activity of *Bordetella* adenylate cyclase-hemolysin against bacterial colonization. *Microb Pathog,* 11, 423-431.

Hackett, M., Guo, L., Shabanowitz, J., Hunt, D. F. and Hewlett, E. L. (1994) Internal lysine palmitoylation in adenylate cyclase toxin from *Bordetella pertussis*. *Science,* 266, 433-435.

Harvill, E. T., Cotter, P. A., Yuk, M. H. and Miller, J. F. (1999) Probing the function of *Bordetella bronchiseptica* adenylate cyclase toxin by manipulating host immunity. *Infect Immun,* 67, 1493-1500.

Hormozi, K., Parton, R. and Coote, J. (1999) Adjuvant and protective properties of native and recombinant *Bordetella pertussis* adenylate cyclase toxin preparations in mice. *FEMS Immunol Med Microbiol,* 23, 273-282.

Ingalls, R. R., Amaout, M. A., Delude, R. L., Flaherty, S., Savedra, R., Jr. and Golenbock, D. T. (1998) The CD11/CD18 integrins: characterization of three novel LPS signaling receptors. *Prog Clin Biol Res,* 397, 107-117.

Karimova, G., Fayolle, C., Gmira, S., Ullmann, A., Leclerc, C. and Ladant, D. (1998) Charge-dependent translocation of *Bordetella pertussis* adenylate cyclase toxin into eukaryotic cells: implication for the in vivo delivery of CD8(+) T cell epitopes into antigen-presenting cells. *Proc Natl Acad Sci U S A,* 95, 12532-12537.

Khelef, N., Bachelet, C. M., Vargaftig, B. B. and Guiso, N. (1994) Characterization of murine lung inflammation after infection with parental *Bordetella pertussis* and mutants deficient in adhesins or toxins. *Infect Immun,* 62, 2893-2900.

Khelef, N. and Guiso, N. (1995) Induction of macrophage apoptosis by *Bordetella pertussis* adenylate cyclase-hemolysin. *FEMS Microbiol Left,* 134, 27-32.

Khelef, N., Sakamoto, H. and Guiso, N. (1992) Both adenylate cyclase and hemolytic activities are required by *Bordetella pertussis* to initiate infection. *Microb Pathog,* 12, 227-235.

Khelef, N., Zychlinsky, A. and Guiso, N. (1993) *Bordetella pertussis* induces apoptosis in macrophages: role of adenylate cyclase-hemolysin. *Infect Immun,* 61, 4064-4071.

Ladant, D., Glaser, P. and Ullmann, A. (1992) Insertional mutagenesis of *Bordetella pertussis* adenylate cyclase. *J Biol Chem,* 267, 2244-2250.

Ladant, D. and Ullmann, A. (1999) *Bordetella pertussis* adenylate cyclase: a toxin with multiple talents. *Trends Microbiol,* 7, 172-176.

Njamkepo, E., Pinot, F., Francois, D., Guiso, N., Polla, B. S. and Bachelet, M. (2000) Adaptive responses of human monocytes infected by *Bordetella pertussis*: the role of adenylate cyclase hemolysin. *J Cell Physiol,* 183, 91-99.

Osicka, R., Osickova, A., Basar, T., Guermonprez, P., Rojas, M., Leclerc, C. and Sebo, P. (2000) Delivery of CD8(+) T-cell epitopes into major histocompatibility complex class I antigen presentation pathway by *Bordetella pertussis* adenylate cyclase: delineation of cell invasive structures and permissive insertion sites. *Infect Immun,* 68, 247-256.

Pearson, R. D., Symes, P., Conboy, M., Weiss, A. A. and Hewlett, E. L. (1987) Inhibition of monocyte oxidative responses by *Bordetella pertussis* adenylate cyclase toxin. *J Immunol,* 139, 2749-2754.

Rogel, A. and Hanski, E. (1992) Distinct steps in the penetration of adenylate cyclase toxin of *Bordetella pertussis* into sheep erythrocytes. Translocation of the toxin across the membrane. *J Biol Chem,* 267, 22599-22605.

Rogel, A., Meller, R. and Hanski, E. (1991) Adenylate cyclase toxin from *Bordetella pertussis*. The relationship between induction of cAMP and hemolysis. *J Biol Chem,* 266, 3154-3161.

Rose, T., Sebo, P., Bellalou, J. and Ladant, D. (1995) Interaction of calcium with *Bordetella pertussis* adenylate cyclase toxin. Characterization of multiple calcium-binding sites and calcium-induced conformational changes. *J Biol Chem,* 270, 26370-26376.

Sambrook, J., Fritsch, E. F. and Maniatis, T. (1989) Molecular cloning: a laboratory manual. Cold Spring Harbor, Plainview, N.Y.

Sebo, P., Glaser, P., Sakamoto, H. and Ullmann, A. (1991) High-level synthesis of active adenylate cyclase toxin of *Bordetella pertussis* in a reconstructed *Escherichia coli* system. *Gene,* 104, 19-24.

Weiss, A. A. and Goodwin, M. S. (1989) Lethal infection by *Bordetella pertussis* mutants in the infant mouse model. *Infect Immun,* 57, 3757-3764.

Wright, S. D., Weitz, J. I., Huang, A. J., Levin, S. M., Silverstein, S. C. and Loike, J. D. (1988) Complement receptor type three (CD11b/CD18) of human polymorphonuclear leukocytes recognizes fibrinogen. *Proc Natl Acad Sci USA,* 85, 7734-7738.

The invention claimed is:

1. A polypeptide capable of binding to CD11b/CD18, said polypeptide consisting of either
   a. a fragment of a *Bordetella* adenylate cyclase having from 30 to 500 amino acids, said fragment comprising the wild-type CD11b/CD18 interaction domain of the *Bordetella* adenylate cyclase, corresponding to amino acid 1166 to amino acid 1281 of SEQ ID NO:1 or SEQ ID NO:3, or comprising a fragment of the wild-type CD11b/CD18 interaction domain sufficient to retain the capacity to bind to CD11b/CD18, or
   b. a variant of said fragment of a *Bordetella* adenylate cyclase, having at least 70% identity with said fragment, wherein said variant retains the capacity to bind to CD11b/CD18.

2. The polypeptide of claim 1, wherein the polypeptide is capable of raising antibodies recognizing *Bordetella* adenylate cyclase, preferably *Bordetella pertussis* adenylate cyclase.

3. The polypeptide according to claim 1, wherein the polypeptide is a fragment of a *Bordetella pertussis* adenylate cyclase, preferably a fragment comprising amino acid 1166 to amino acid 1281 of *Bordetella pertussis* adenylate cyclase, and more preferably a fragment comprising amino acid 1208 to amino acid 1243 of *Bordetella pertussis* adenylate cyclase.

4. The polypeptide according to claim 3, which further comprises an acylation domain of adenylate cyclase and/or the hydrophobic domain.

5. The polypeptide according to claim 4, wherein the polypeptide is not toxic when administered in vivo to a mammal.

6. A method for the prevention or treatment, in human or in an animal, of disease symptoms associated with whooping cough and/or for protecting a human or an animal against the disease symptoms associated with *Bordetella* infection, wherein the method comprises administering to the human or animal an effective amount of the polypeptide of claim 1.

7. A vector for targeting a molecule of interest to CD11b/CD18 expressing cells, wherein the vector comprises the polypeptide capable of binding to CD11b/CD18 according to claim 1, coupled to a molecule of interest.

8. The vector according to claim 7, wherein said molecule of interest is selected among the group consisting of: peptides, glycopeptides, lipopeptides, polysaccharides, oligosaccharides, nucleic acids, lipids and chemicals.

9. The vector according to claim 7 or 8, wherein said molecule of interest is the active principle of a medicament.

10. The vector according to claim 7, wherein said molecule of interest is coupled by chemical linkage.

11. The vector according to claim 7, wherein said molecule of interest comprises an antigen or an epitope.

12. The vector according to claim 11, wherein said molecule of interest is a peptide or a polypeptide comprising an antigen or an epitope.

13. A composition comprising the polypeptide according to claim 1 or the vector of claim 7, in combination with a pharmaceutically acceptable vehicle.

14. A composition comprising the vector according to claim 11, in combination with a pharmaceutically acceptable vehicle.

15. The composition of claim 14, wherein said composition comprises an adjuvant.

16. The polypeptide of claim 1, wherein the wild-type CD11b/CD18 interaction domain consists of SEQ ID NO: 2.

17. The polypeptide of claim 1, wherein the wild-type CD11b/CD18 interaction domain consists of SEQ ID NO: 4.

* * * * *

UNITED STATES PATENT AND TRADEMARK OFFICE
CERTIFICATE OF CORRECTION

| | | |
|---|---|---|
| PATENT NO. | : 7,906,123 B1 | Page 1 of 1 |
| APPLICATION NO. | : 11/713708 | |
| DATED | : March 15, 2011 | |
| INVENTOR(S) | : Claude Leclerc et al. | |

It is certified that error appears in the above-identified patent and that said Letters Patent is hereby corrected as shown below:

Title Page, item (73), lines 1-2, "Centre National de la Recherche Scientique" should read
--Centre National de la Recherche Scientifique--.

Signed and Sealed this
Seventeenth Day of May, 2011

David J. Kappos
*Director of the United States Patent and Trademark Office*